United States Patent
Omote

(10) Patent No.: US 7,257,192 B2
(45) Date of Patent: Aug. 14, 2007

(54) METHOD AND APPARATUS FOR X-RAY REFLECTANCE MEASUREMENT

(75) Inventor: Kazuhiko Omote, Akiruno (JP)

(73) Assignee: Rigaku Corporation, Tokyo (JP)

( * ) Notice: Subject to any disclaimer, the term of this patent is extended or adjusted under 35 U.S.C. 154(b) by 99 days.

(21) Appl. No.: 11/178,773

(22) Filed: Jul. 11, 2005

(65) Prior Publication Data

US 2006/0013362 A1    Jan. 19, 2006

(30) Foreign Application Priority Data

Jul. 15, 2004    (JP) .............................. 2004-209074

(51) Int. Cl.
*G01N 23/20* (2006.01)

(52) U.S. Cl. ..................... 378/70; 378/81; 378/84; 378/89

(58) Field of Classification Search ............. 378/70–90
See application file for complete search history.

(56) References Cited

U.S. PATENT DOCUMENTS

| 6,577,705 | B1 | 6/2003 | Chang et al. |
| 2004/0190681 | A1 | 9/2004 | Omote |

FOREIGN PATENT DOCUMENTS

| EP | 1 462 795 A2 | 9/2004 |
| JP | 11-258185 A | 9/1999 |
| JP | 2000-035408 A | 2/2000 |
| JP | 3109789 B2 | 9/2000 |
| JP | 3468623 B2 | 9/2003 |
| JP | 3504539 B2 | 12/2003 |
| JP | 2004-093521 A | 3/2004 |

OTHER PUBLICATIONS

K. Omote & K. Inaba. "Thin Film Evaluation Method Using Glazing Incidence X-ray Diffraction", Analysis, Japan Society for Analytical Chemistry, 2002, vol. 11, pp. 623-629.

C. Zakri et al. "Determination of the In-Plane Elastic Tensor of Crystalline Decanol Monolayers on Water by X-ray Diffraction", The American Physical Society, 1997, Physical Review B, vol. 55, No. 21, Jun. 1, 1997—entire document.

*Primary Examiner*—Jurie Yun
(74) *Attorney, Agent, or Firm*—Frishauf, Holtz, Goodman & Chick, P.C.

(57) ABSTRACT

In a method for X-ray reflectance measurement in which an intensity of a reflected X-ray is observed for each incident angle, a measuring scale for the incident angle ω is corrected, before the reflectance measurement, using an analyzer crystal. In the corrective operation, the aperture width of the receiving slit is made wider than in the X-ray reflectance measurement, and the analyzer crystal is inserted in the reflection path, and then the reflected X-ray intensity is detected. In this condition, the incident angle ω of the incident X-ray to the sample surface can be determined accurately, and thus the measuring scale for the incident angle can be corrected. Thereafter, the analyzer crystal is removed from the reflection path, and the X-ray reflectance measurement for the sample surface is carried out.

5 Claims, 23 Drawing Sheets

FIG. 2

$$D = \frac{\delta W}{\sin \omega} \tag{1}$$

$$\tan \delta (2\theta) = \frac{D \sin 2\theta m}{L - D \cos 2\theta m} \tag{2}$$

$$\delta (2\theta) = \frac{\delta W}{\sin \omega} \frac{\sin 2\theta m}{L} \tag{3}$$

$$\omega a = \frac{2\theta a}{2} = \frac{2\theta m + \delta(2\theta)}{2} \tag{4}$$

$$\omega m = \frac{2\theta m}{2} \neq \omega a \tag{5}$$

$$2\theta a = 2\theta m \quad (6)$$

$$\omega a = \frac{2\theta a}{2} = \frac{2\theta m}{2} \rightarrow \omega m \quad (7)$$

FIG. 17

PRIOR ART

Analysis results by prior art method

| W (mm) | Density (g/cm$^3$) | Thickness (nm) |
|--------|--------------------|----------------|
| 10.003 | 1.1133 | 734.855 |
| 10.013 | 1.1413 | 733.88 |
| 10.023 | 1.166 | 732.216 |

FIG. 20

Analysis results by present invention

| W (mm) | Density (g/cm$^3$) | Thickness (nm) |
|---|---|---|
| 10.003 | 1.1342 | 733.524 |
| 10.013 | 1.1391 | 734.01 |
| 10.023 | 1.1353 | 734.754 |

METHOD AND APPARATUS FOR X-RAY REFLECTANCE MEASUREMENT

BACKGROUND OF THE INVENTION

1. Field of the Invention

The present invention relates to a method and an apparatus for measuring a reflectance of specular reflection, i.e., total reflection, of an X-ray which is reflected by a surface of a sample, and especially to a method and an apparatus for X-ray reflectance measurement in which a correct value of an incident angle to the sample surface can be determined accurately to realize high-accurate reflectance measurement.

2. Description of the Related Art

Some methods are known for measuring a thickness of a thin film deposited on a substrate. Of these methods, an X-ray reflectance method is in the spotlight because it can determine the absolute value of the thickness and also it is nondestructive. Although the X-ray reflectance method has the advantages of the determination of the absolute value of the thickness and the nondestructive measurement, the observed thickness determined by the current X-ray reflectance method is said to be inferior, in view of repeatability, to that obtained by the X-ray photoelectron spectroscopy method or the ellipsometry method. If the repeatability of the thickness is improved in the X-ray reflectance method, the X-ray reflectance method could be the hopeful standard method for the thickness measurement.

There are many publications disclosing the determination of the thickness and/or the density of the thin film with the use of the X-ray reflectance method, the examples being Japanese patent publication No. 2000-35408 A and Japanese patent publication No. 11-258185 A (1999).

The inferior repeatability of thickness in the X-ray reflectance method is attributed to inaccurate determination of the incident angle of the incident X-ray which is incident on the surface of the thin film sample. It will be explained in detail below.

FIG. 1A is a plan view showing an X-ray path under the condition in which the X-ray optical system of the X-ray reflectance measurement apparatus is in the state of $2\theta=0$. Defining an angle of the reflected X-ray to the incident X-ray 10, i.e., a scattering angle, as $2\theta$, the state of $2\theta=0$ can be said to be the state in which the incident X-ray 10 is directly incident on an X-ray detector 12. The incident X-ray 10 has been positioned so as to pass through the center O of the goniometer. The X-ray detector 12 can rotate around the goniometer center O and its rotation angle is $2\theta$. An angle of incident X-ray 10 to the surface of a sample 16 is defined as an incident angle $\omega$. The sample 16 also can rotate around the goniometer center O and its rotation angle is equal to $\omega$. The position of the sample 16 is adjusted, with the use of the conventional half-split method, so as to allow its surface to coincide with the goniometer center O. If the surface of the sample 16 is positioned just on the goniometer center O, the incident angle $\omega$ is accurately equal to the rotation angle of the sample 16, so that the accuracy of the observed incident angle $\omega$ would be the same as the accuracy of the angle determination of the drive mechanism for the rotation of the sample 16. It is very difficult, however, from a practical standpoint to allow the position of the sample surface to coincide with the goniometer center O with accuracy of less than one micrometer. Discussing the error $\delta W$ in positioning the sample 16, this error $\delta W$ is expressed by a distance between the goniometer center O and the surface of the sample 16. The existence of such error $\delta W$ causes deterioration in accuracy of the observed incident angle $\omega$.

FIG. 1B shows a condition in which an X-ray reflectance is measured for the sample 16 having the above-described positioning error $\delta W$. The X-ray reflectance is measured with the following steps: the sample 16 is rotated in $\omega$-rotation while the X-ray detector 12 is rotated in $2\theta$-rotation with a relationship of $\omega: 2\theta=1:2$; and an X-ray intensity of the specular reflection, i.e., total reflection, from the surface of the sample 16 is detected. Defining the observed value of the scattering angle $2\theta$ as $2\theta m$, the angle $2\theta m$ is equal to the rotation angle of the X-ray detector 12 around the goniometer center O. A receiving slit 18 is disposed in front of the X-ray detector 12 and is rotated synchronously with the X-ray detector 12. The aperture width of the receiving slit 18 is set to be narrow. The scattering angle $2\theta m$ of the specular reflection is very small, usually less than several degrees, or over ten degrees at largest. The rotation angle $\omega$ of the sample 16, i.e., the incident angle $\omega$, is scanned within a small range in the vicinity of the half of $2\theta m$, so that the intensity of a reflected X-ray 20 detected by the X-ray detector 20 varies and the observed incident angle $\omega$ can be determined at the maximum intensity. Then, the observed incident angle $\omega$ is scanned, i.e., the scattering angle $2\theta$ is scanned, to obtain the intensity of the reflected X-ray for each incident angle. The reflected X-ray intensities are plotted versus the incident angles to make an X-ray reflectance curve.

Defining a real incident angle of the incident X-ray 10 to the sample surface as $\omega a$, it is difficult to know the real incident angle $\omega a$ with high accuracy, because it is difficult, with measurement, to determine the origin of the incident angle $\omega$ with high accuracy, the origin being defined as the condition in which the incident X-ray 10 becomes perfectly parallel to the sample surface. Then, in the conventional method, it has been assumed that the real incident angle $\omega a$ is equal to the half of the observed value $2\theta m$ of the scattering angle $2\theta$, because, in principle in the specular reflection, the incident angle is just equal to the half of the scattering angle.

However, since there exits the positioning error $\delta W$ of the sample 16 as described above, the observed value $2\theta m$ of the scattering angle is different from the real scattering angle $2\theta a$. Now, the difference between $2\theta m$ and $2\theta a$ is expressed by $\delta(2\theta)$, that is, $2\theta a=2\theta m+\delta(2\theta)$. The observed value $2\theta m$ is an angle measured around the goniometer center O, while the real scattering angle is an angle of the reflected X-ray 20 to the incident X-ray 10 around the real X-ray irradiation point P on the sample surface. The direction of the reflected X-ray 20, i.e., the angle of the reflected X-ray 20, is determined by the position of the receiving slit 18. The distance D between the goniometer center O and the X-ray irradiation point P causes the above-described difference $\delta(2\theta)$.

Estimation for $\delta(2\theta)$ will be explained below. The distance D is found with formula (1) in FIG. 2. A tangent of the difference $\delta(2\theta)$ is found with formula (2) in FIG. 2, noting that L is the distance between the goniometer center O and the receiving slit 18. Since $\delta(2\theta)$ is very small, $\tan \delta(2\theta)$ is almost equal to $\delta(2\theta)$, provided that $\delta(2\theta)$ is expressed in units of radian. Thus, the left side of formula (2) becomes $\delta(2\theta)$. On the other hand, in the right side of formula (2), since D is much smaller than L, the denominator is almost equal to L. Therefore, formula (2) comes near to formula (3).

As shown in formula (4), the real incident angle $\omega a$ is just equal to the half of the real scattering angle $2\theta a$ which is different from the observed value $2\theta m$ by the difference $\delta(2\theta)$. Accordingly, if the incident angle is determined based on $2\theta m$ (the thus-determined incident angle being referred to as ωm hereinafter), the observed incident angle ωm is different from the real incident angle ωa as shown in formula (5). In the conventional method, a reflectance curve is obtained based on the observed incident angle ωm which is different from the real incident angle ωa, and then the thickness of the thin film is determined based on the reflectance curve, resulting in insufficient repeatability of the thickness measurement.

The value of δ(2θ) will be discussed with applying suitable values to the above-described formula (3). The positional error δW of the sample is assumed to be one micrometer. If the position of the sample is adjusted with the usual half-split method, the positional error would be not so large, but it is difficult to position the sample with accuracy of less than one micrometer. The angle 2θm is assumed to be 0.6 degree, and the angle ω is assumed to be 0.3 degree which is the half of 2θm. These values are applied to formula (3) to result in that δ(2θ) becomes about $1.0 \times 10^{-5}$ radian, which corresponds to about two second in angle. Although the two second is a very small angle, the angular error to such an extent would have a problem in determining the thickness of the thin film with a good repeatability using the X-ray reflectance method. Especially, it is an important problem in the conventional method that there is no means for verifying how much the difference δ(2θ) is.

SUMMARY OF THE INVENTION

It is an object of the present invention to provide a method for X-ray reflectance measurement, in which intensities of reflected X-rays are measured for respective incident angles, having improved accuracy and improved repeatability in determining the incident angles.

A method for X-ray reflectance measurement according to the present invention is characterized in that a measuring scale for the incident angle ω is corrected using an analyzer crystal. After the correction of the measuring scale, the analyzer crystal is removed and then X-ray reflectance measurement is carried out. That is, a method for X-ray reflectance measurement according to the present invention comprises the steps of: (a) preparing an apparatus for X-ray reflectance measurement including: an X-ray source for generating an incident X-ray which can pass through a reference point; a sample holder for holding a sample so as to allow a surface of the sample to coincide with the reference point as best as possible; an X-ray detector for detecting an intensity of a reflected X-ray which is generated under a condition in which the incident X-ray is reflected by the sample surface under specular reflection; incident-angle-changing means for changing an angle ω between the incident X-ray and the sample surface around the reference point which is a center of angle change, the angle ω being referred to as an incident angle hereinafter; and scattering-angle-changing means for changing an angle 2θ between the incident X-ray and a direction of the reflected X-ray which goes off the sample surface to be detected by the X-ray detector around the reference point which is a center of angle change, the angle 2θ being referred to as a scattering angle hereinafter; (b) arranging an analyzer crystal in a reflection path connecting the reference point and the X-ray detector, and adjusting a position of the X-ray detector with respect to the analyzer crystal so as to allow the reflected X-ray having a certain wavelength which has been reflected by the analyzer crystal to be properly detected by the X-ray detector; (c) setting the scattering angle 2θ to zero degree with a use of the scattering-angle-changing means to make a first condition in which the incident X-ray passes through the reference point with no collision with the sample and is reflected by the analyzer crystal and is thereafter detected by the X-ray detector, and adjusting an angle of the analyzer crystal with respect to the incident X-ray so as to allow an X-ray intensity detected by the X-ray detector to become maximum; (d) (i) setting the scattering angle 2θ to a predetermined reference angle 2θr with a use of the scattering-angle-changing means with a positional relationship, between the analyzer crystal and the X-ray detector, remaining as it is, (ii) adjusting a position of the sample so as to allow the sample surface to coincide with the reference point as precisely as possible, (iii) irradiating the sample surface with the incident X-ray, (iv) adjusting an incident angle ω with a use of the incident-angle-changing means so as to allow an X-ray intensity of the reflected X-ray detected by the X-ray detector to become maximum, the reflected X-ray to be detected being one generated in a condition in which the incident X-ray is reflected by the sample surface under specular reflection and is further reflected by the analyzer crystal, and (v) correcting a measuring scale for the incident angle ω so as to allow a observed value of the incident angle ω to become perfectly a half of the reference angle 2θr; (e) removing the analyzer crystal from the reflection path to bring a position of the X-ray detector back to a condition without the analyzer crystal; and (f) measuring an X-ray reflectance of the sample, the measuring step including the steps of: changing the incident angle ω to plural values on a basis of the corrected measuring scale; irradiating the sample surface with the incident X-ray at each value of the incident angle ω; and detecting an intensity of the reflected X-ray by the X-ray detector at each value of the incident angle ω.

An apparatus for X-ray reflectance measurement according to the present invention is an apparatus for carrying out the above-described method for X-ray reflectance method, and comprises: (a) an X-ray source for generating an incident X-ray which can pass through a reference point; (b) a sample holder for holding a sample so as to allow a surface of the sample to coincide with the reference point as best as possible; (c) an X-ray detector for detecting an intensity of a reflected X-ray which is generated under a condition in which the incident X-ray is reflected by the sample surface under specular reflection; (d) incident-angle-changing means for changing an angle ω between the incident X-ray and the sample surface around the reference point which is a center of angle change, the angle ω being referred to as an incident angle hereinafter; (e) scattering-angle-changing means for changing an angle 2θ between the incident X-ray and a direction of the reflected X-ray which goes off the sample surface to be detected by the X-ray detector around the reference point which is a center of angle change, the angle 2θ being referred to as a scattering angle hereinafter; (f) an analyzer crystal capable of being inserted in and being removed from a reflection path connecting the reference point and the X-ray detector; (g) means for (i) adjusting a position of the X-ray detector so as to properly detect the reflected X-ray which has been reflected by the analyzer crystal when the analyzer crystal is inserted in the reflection path and (ii) adjusting a position of the X-ray detector so as to properly detect the reflected X-ray which has been reflected by the sample when the analyzer crystal is removed from the reflection path; and (h) means for adjusting an attitude angle of the analyzer crystal so as to allow the incident X-ray to be reflected by the analyzer crystal.

The present invention has the advantage that even if the positioning error of the sample exists, the real incident angle is determined with the use of the analyzer crystal so that the measuring scale for the incident angle can be corrected to coincide with the real incident angle. Accordingly, the X-ray reflectance measurement has improved accuracy and improved repeatability in determining the incident angle and can obtain a reflection curve with high accuracy.

BRIEF DESCRIPTION OF THE DRAWINGS

FIG. 2 shows formulae regarding the angular difference δ(2θ) which is caused by the positional error δW of the sample;

FIG. 17 shows a table indicating densities and thicknesses which are determined based on the reflectance curves shown in FIGS. 15 and 16;

FIG. 20 shows a table indicating densities and thicknesses which are determined based on the reflectance curves shown in FIGS. 18 and 19;

DETAILED DESCRIPTION OF THE PREFERRED EMBODIMENTS

Figure 3:
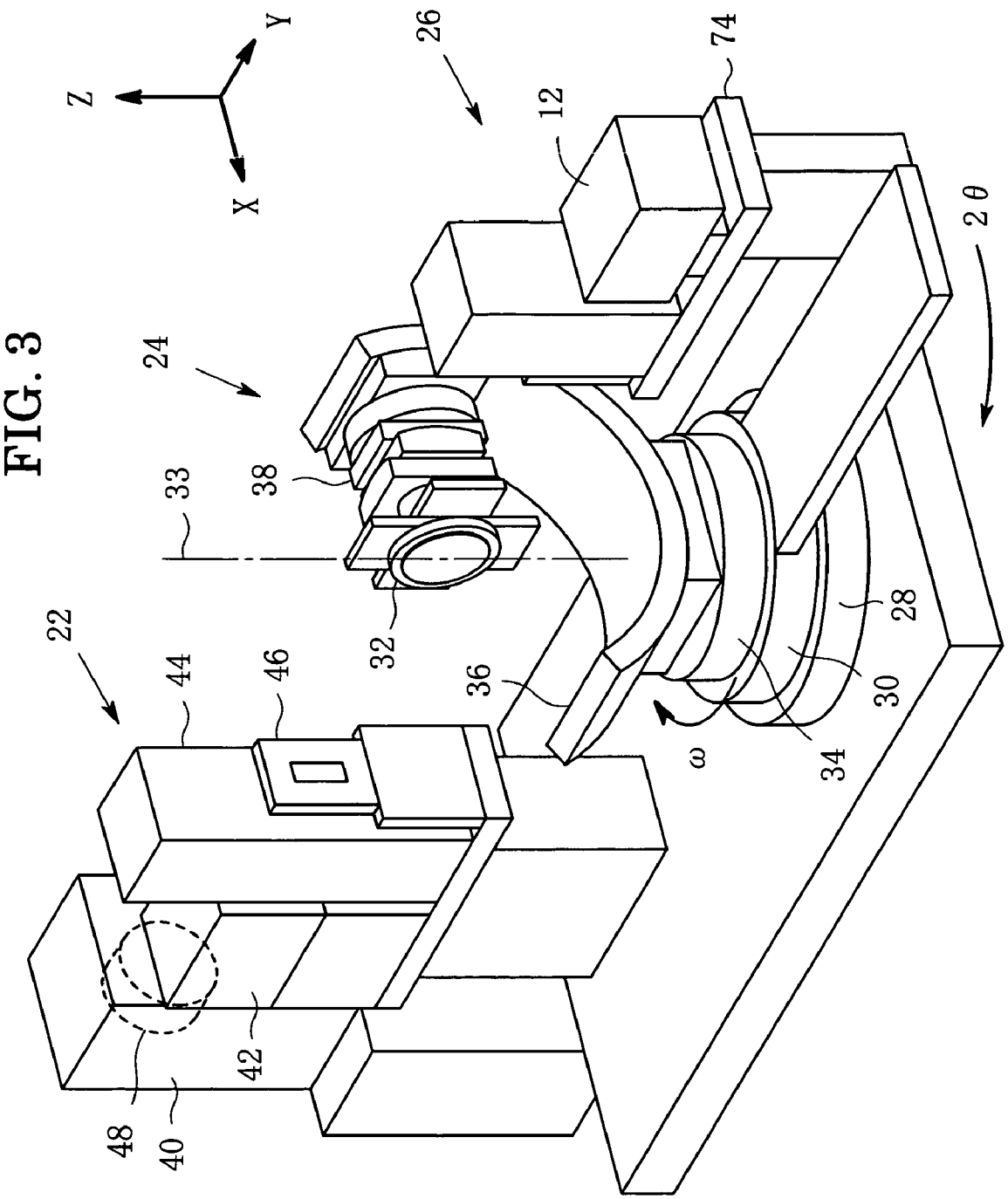
FIG. 3 is a perspective view illustrating one example of an apparatus for X-ray reflectance measurement according to the present invention.

An embodiment of the present invention will now be described below with reference to the drawings. FIG. 3 is a perspective view showing one embodiment of an apparatus for X-ray reflectance measurement according to the present invention. The apparatus for X-ray reflectance measurement is comprised of an incident optical system 22, a sample support mechanism 24 and a receiving optical system 26.

The sample support mechanism 24 has a sample holder 32 whose surface stands upright. The sample support mechanism 24 has an ω-turntable 34 which can turn around an axis of rotation 33 with respect to a base 28. This rotation will be referred to as an ω-rotation. On the other hand, a 2θ-turntable 30 which supports the receiving optical system 26 also can turn around the axis of rotation 33 with respect to the base 28. The rotation of the 2θ-turntable 30 will be referred to as a 2θ-rotation. The 2θ-turntable 30 and the ω-turntable 34 can turn independently of one another. A mechanism for each rotation is a high-resolution rotation control mechanism with angular repeatability of 0.00002 degree. Angular control for such a rotation is established by an encoder control using a servomotor. The ω-turntable 34 and the 2θ-turntable 30 constitute a goniometer whose center coincides with the above-described axis of rotation 33. The goniometer center, i.e., the axis of rotation 33, corresponds to the reference point in the present invention. The drive mechanism for the ω-turntable 34 corresponds to the incident-angle-changing means in the present invention while the drive mechanism for the 2θ-turntable 30 corresponds to the scattering-angle-changing means in the present invention.

Figure 4:
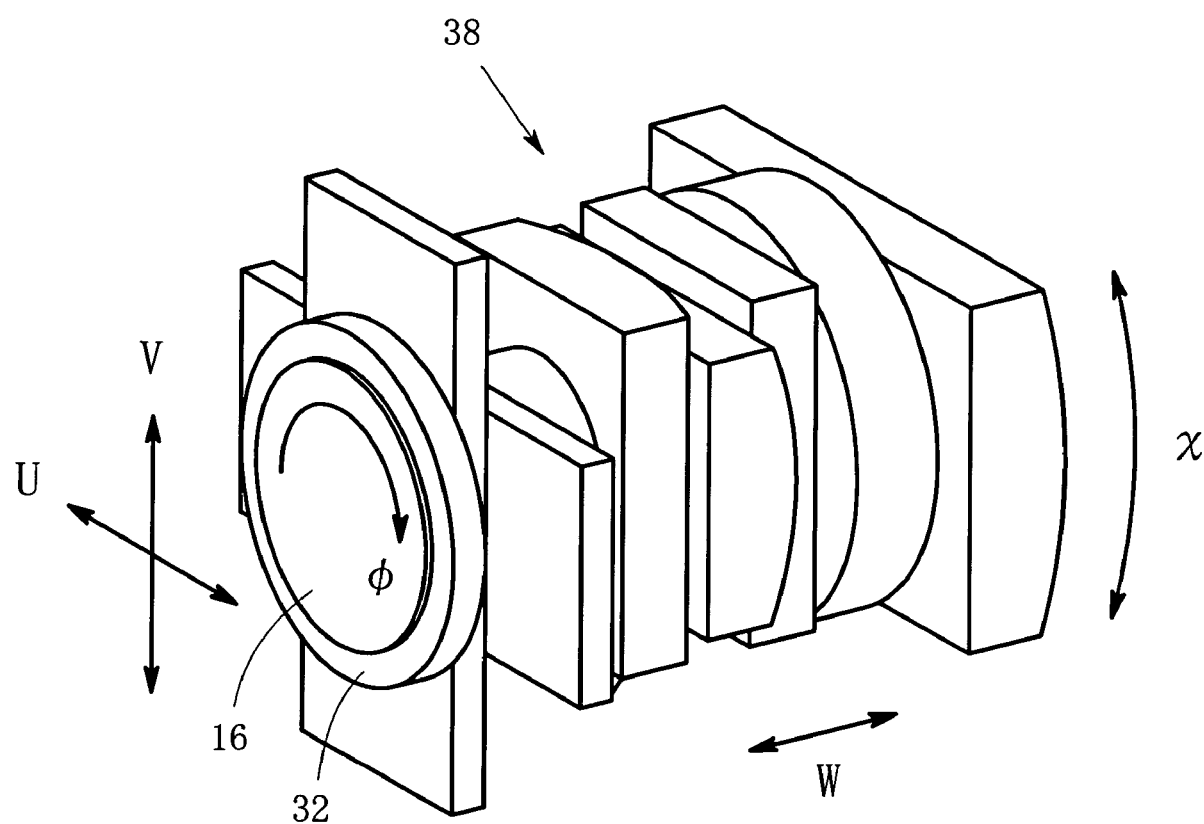
FIG. 4 is a perspective view of a sample drive mechanism.

A curved guide 36 is fixed on the ω-turntable 34. A sample drive mechanism 38 is mounted on the curved guide 36. The sample drive mechanism 38, as shown in FIG. 4, allows the sample holder 32 to move in a U-direction, in a V-direction and in a W-direction and also to turn in φ-rotation and in χ (chi in Greek alphabet)-rotation. The movements in the U-direction and the V-direction are to give the sample 16 a two-dimensional movement in a plane which includes the sample 16, and are used for changing the X-ray irradiation point on the surface of the sample 16. The movement in the W-direction is to allow the sample 16 to move in the normal direction to the surface of the sample 16, and is used to allow the surface of the sample 16 to coincide with the goniometer center. The φ-rotation gives the sample 16 an in-plane rotation. The χ-rotation is for adjusting the tilt angle of the sample 16.

Figure 5:
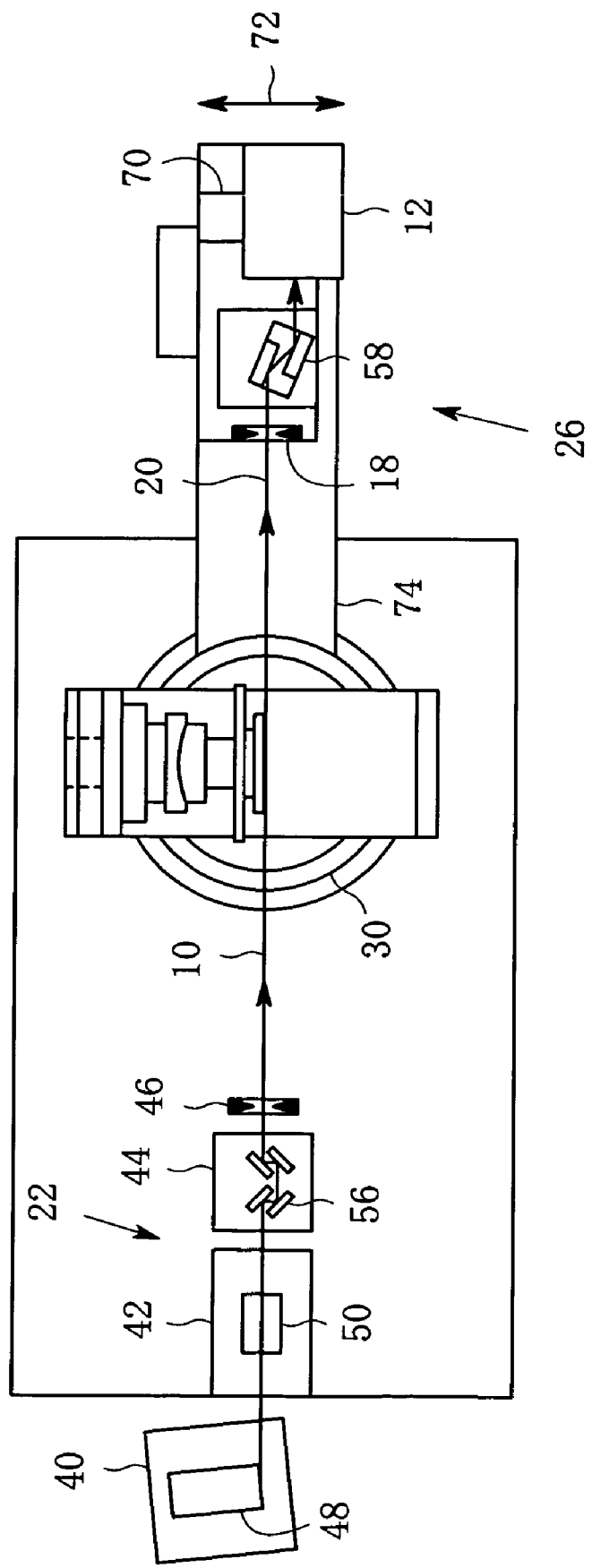
FIG. 5 is a plan view of the apparatus for X-ray reflectance measurement shown in FIG. 3.

FIG. 5 is a plan view of the apparatus for X-ray reflectance measurement shown in FIG. 3. Referring to FIGS. 3 and 5, the incident optical system 22 includes an X-ray tube 40, a multilayer mirror device 42, an incident-monochromator device 44, and an incident slit 46. The X-ray tube 40 includes a rotating target 48, which revolves around a horizontal axis of rotation for generating an X-ray with a point focus. The multilayer mirror device 42 accommodates a multilayer mirror 50 therein.

Figure 6:
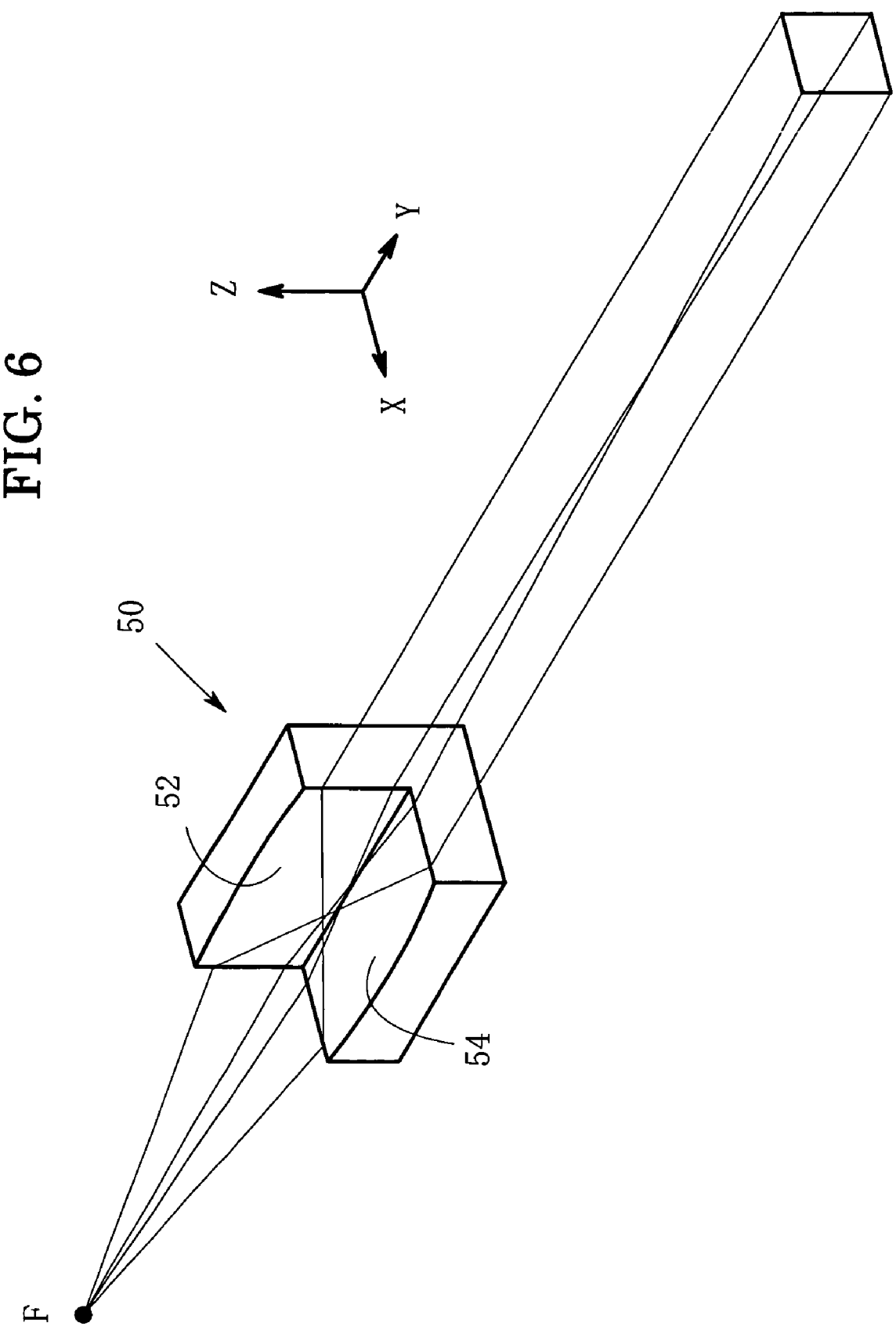
FIG. 6 is a perspective view of a multilayer mirror.

The multilayer mirror 50 includes, as shown in FIG. 6, a first mirror having a first parabolic reflective surface 52 made of synthetic multilayer films and a second mirror having a second parabolic reflective surface 54 made of synthetic multilayer films so as to form a multilayer mirror having a so-called side-by-side structure in that the first and second mirrors are joined to each other at their sides at an angle of about 90 degrees. Using the multilayer mirror 50, an X-ray beam (diverging beam) emitted from an X-ray focus F of the X-ray tube can be collimated within the X-Y plane as well as within the Y-Z plane. An X-ray reflected at the first reflective surface 52 at first is further reflected at the second reflective surface 54 and goes out. On the other hand, an X-ray reflected at the second reflection surface 54 at first is further reflected at the first reflection surface 52 and goes out. The first reflective surface 52 collimates the X-ray in the X-Y plane while the second reflective surface 54 collimates the X-ray in the Y-Z plane. The X-ray beam diverging from the X-ray focus F is collected on the parabolic surface and collimated, so that a parallel beam can be obtained with a high intensity. Using this multilayer mirror, a divergence angle of an X-ray can be reduced within a range of 0.04 degree, for example. If the collimation is insufficient with the use of the multilayer mirror only, the incident monochromator device may be used, as will be described later. It is noted that the multilayer mirror is not essential in the present invention but may be omitted.

Referring back to FIG. 5, the incident-monochromator device 44 includes a plurality of monochromators therein, and these monochromators can be switched for use. FIG. 5 shows a state in that a four-crystal monochromator 56 is used. Using the incident-monochromator device 44, an incident X-ray is made monochromatic in addition to the collimation.

Figure 7:
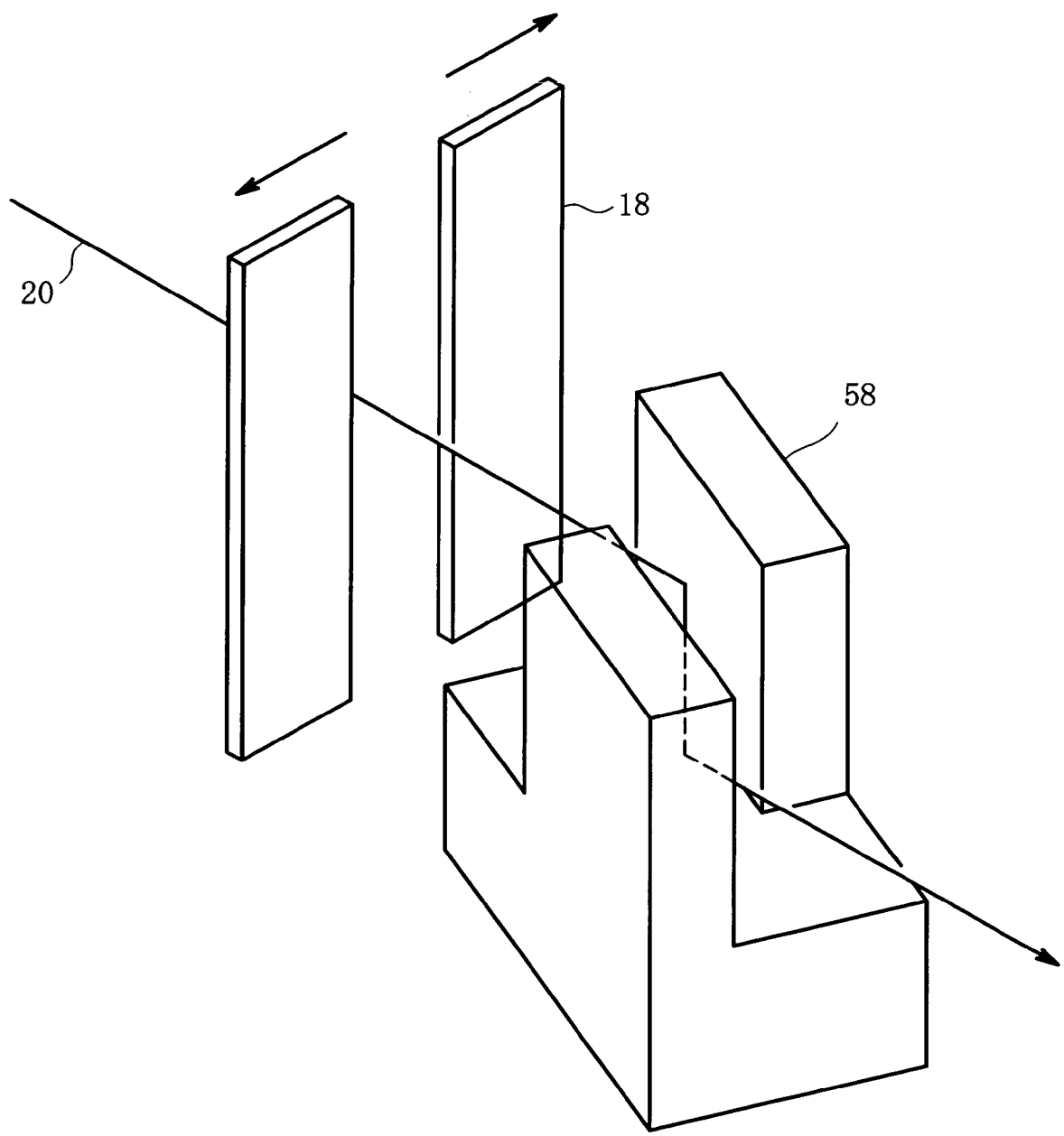
FIG. 7 is a perspective view showing an analyzer crystal and a receiving slit.
Figure 8:
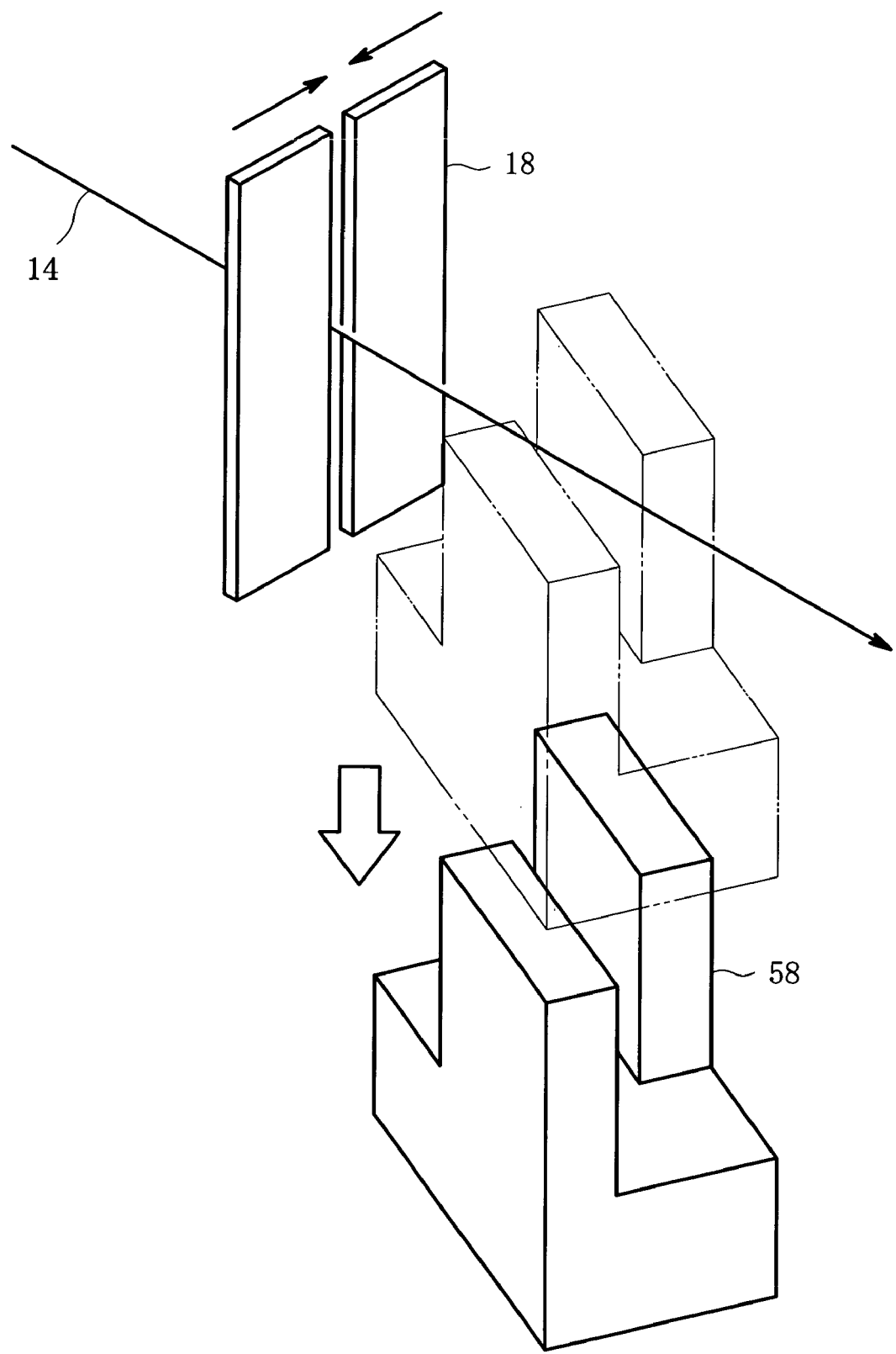
FIG. 8 is a perspective view showing another state of the analyzer crystal and the receiving slit.

Next, a receiving optical system will be described. Referring to FIG. 5, the receiving optical system 26 includes a receiving slit 18, an analyzer crystal 58, and an X-ray detector 12. FIG. 7 is a perspective view showing the analyzer crystal 58 and the receiving slit 18. The analyzer crystal 58 is a channel-cut crystal which has two reflective surfaces parallel to each other and uses a Ge(220) plane as a reflective surface. The reflected X-ray 20 passes through the receiving slit 18 and is then reflected twice by the analyzer crystal 58 to go for the X-ray detector. The analyzer crystal 58 is movable vertically. When the analyzer crystal 58 is in the upper position, as shown in FIG. 7, to be inserted in the X-ray path, the reflected X-ray 20 is reflected by the analyzer crystal 58. On the other hand, when the analyzer crystal 58 is in the lower position, as shown in FIG. 8, to be removed from the X-ray path, the reflected X-ray 20 is not reflected by the analyzer crystal 58 but goes straight for the X-ray detector.

The analyzer crystal 58 may not be the channel-cut crystal. In principle, the analyzer crystal may be any monochromator which uses the Bragg's reflection, such as a flat-plate monochromator.

Figure 9:
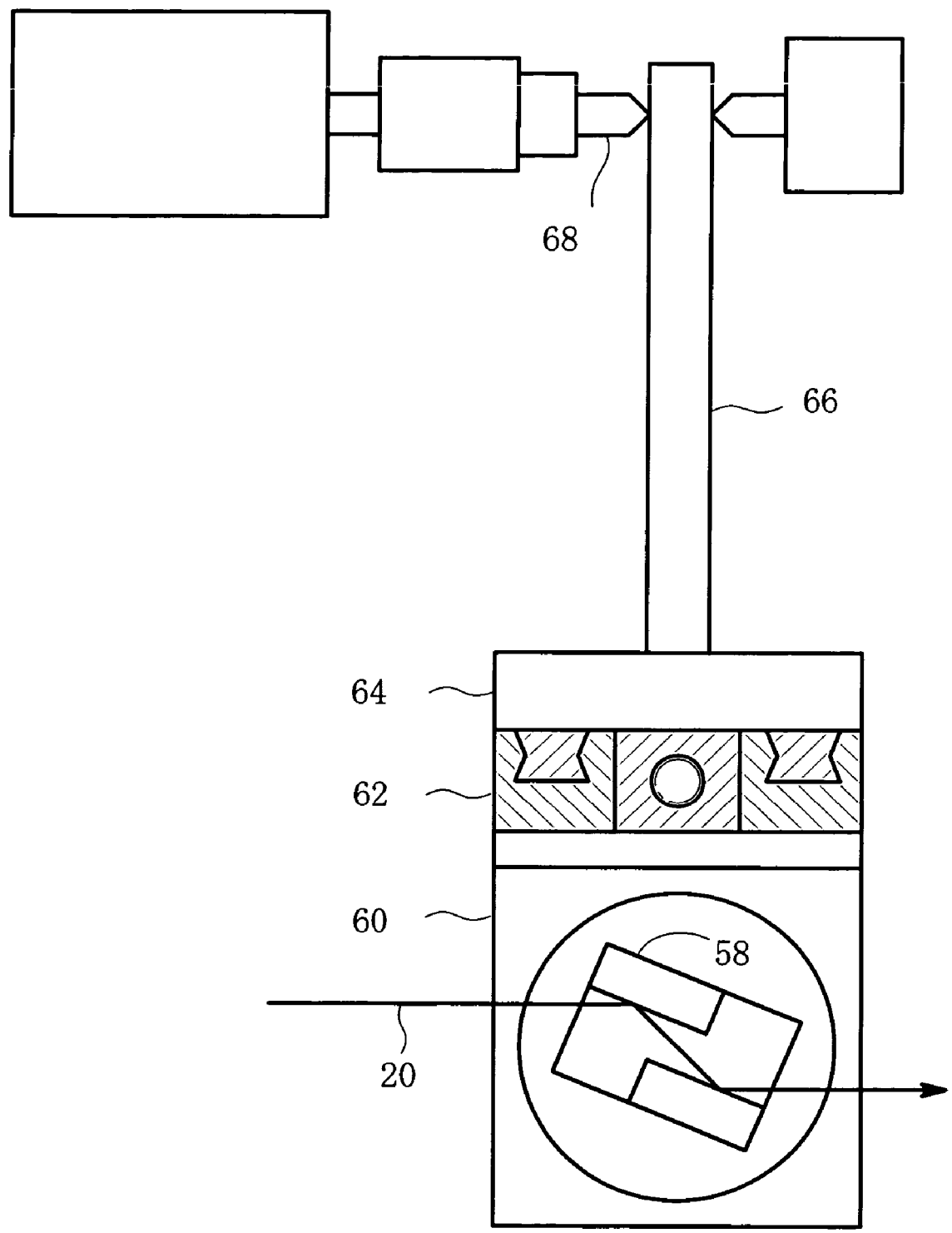
FIG. 9 is a plan view showing a fine adjustment mechanism for the attitude angle of the analyzer crystal.

FIG. 9 is a plan view of a fine adjustment mechanism for the attitude angle of the analyzer crystal. The analyzer crystal 58 is mounted on a crystal support table 60, which is fixed to an elevating mechanism 62 that is movable up and down along an elevating guide 64. A sine-bar 66 has a root which is fixed to the elevating guide 64, which can turn by a very small angle. An end of the sine-bar 66 is pushed by a pushrod 68, so that the rotation of the elevating guide 64 allows the crystal support table 60 to turn, resulting in the fine adjustment of a rotational angle of the analyzer crystal 58 so as to take out the reflected X-ray 20 properly. Assuming that the length of the sine-bar 66 is 100 mm, for example, the adjustment is possible with accuracy in angle not more than 0.0001 degree.

Referring back to FIG. 5, the X-ray detector 12 is a scintillation counter, which can be moved in a direction perpendicular to the optical axis of the receiving optical system 26 along a guide 70, as indicated by an arrow 72. Since the spatial location at which the reflected X-ray 20 is incident on the X-ray detector 12 is different between one state in which the analyzer crystal 58 is inserted in the line of the reflected X-ray and another state in which the analyzer crystal 58 is removed from the line, the X-ray detector 12 must be shifted, in response to whether or not the analyzer crystal 58 is used, in a direction denoted by an arrow 72 in FIG. 5.

The receiving slit 18, the analyzer crystal 58 and the X-ray detector 12 are mounted on a detector support table 74, which is fixed to the 2θ-turntable 30. When the 2θ-turntable 30 turns in 2θ-rotation, the receiving optical system 26 is to turn in 2θ-rotation as a whole.

Figure 10A:
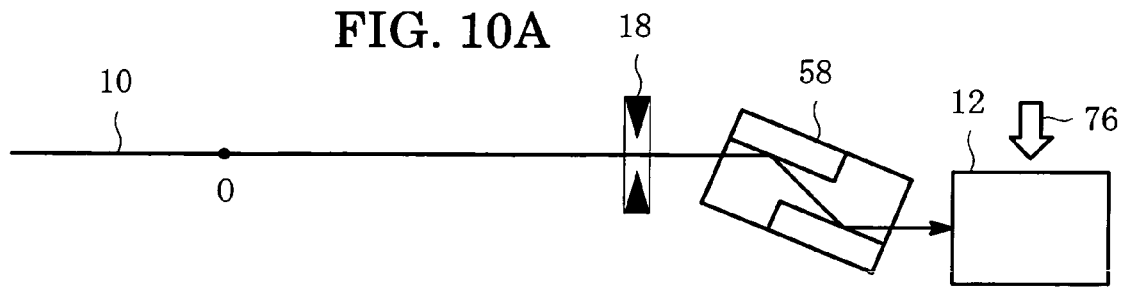
FIGS. 10A, 10B and 10C are plan views of the X-ray optical system for explaining the principle of the method for X-ray reflectance measurement according to the present invention.
Figure 10B:
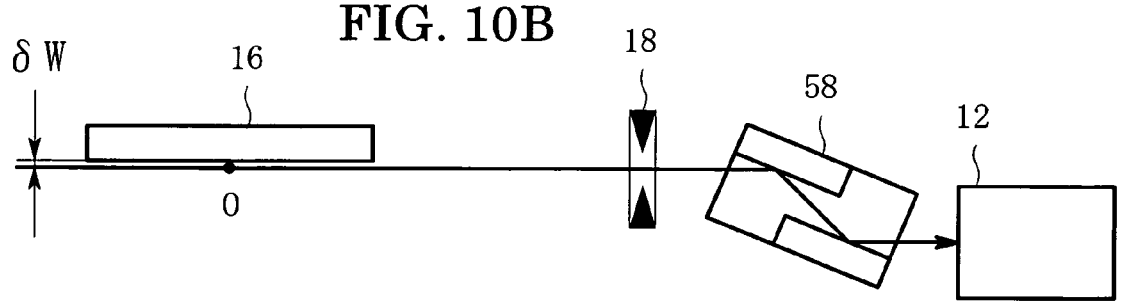
Figure 10C:
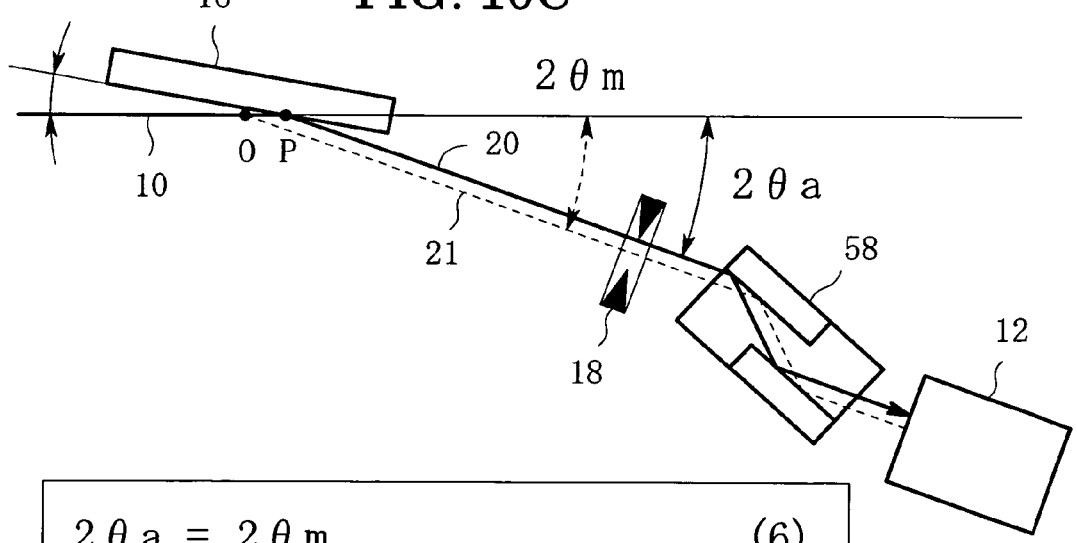
Figure 11:
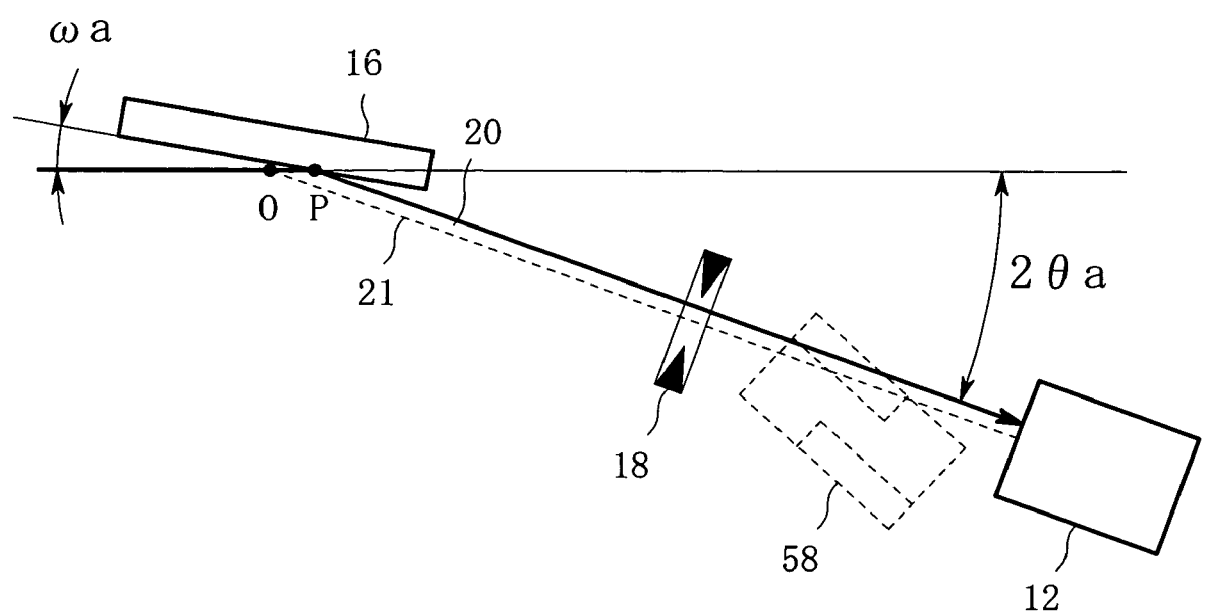
FIG. 11 is a plan view showing another state of the X-ray optical system shown in FIG. 10C.

Next, the principle of the method for X-ray reflectance measurement according to the present invention will be described. FIGS. 10A, 10B, 10C and 11 are plan views each showing an X-ray optical system for explaining the principle. FIGS. 10A to 10C show a step for correcting a measuring scale for the incident angle, while FIG. 11 shows another step, following the correction step, for measuring an X-ray reflectance.

Referring to FIG. 10A, the 2θ-turntable 30 (see FIG. 3) is allowed to turn to the position of 2θ=zero degree, at first. Then, the analyzer crystal 58 is inserted in the X-ray path. The X-ray detector 12 is shifted in the direction denoted by the arrow 76 so as to detect an X-ray which has been reflected by the analyzer crystal 58. The receiving slit 18 is allowed to have a wide aperture width as shown in FIG. 7, unlike with the usual X-ray reflectance measurement. Assuming that the beam width of the incident X-ray which is incident on the sample is 0.1 mm for instance, the aperture width of the receiving slit 18 may be 0.1 to 0.2 mm for the usual X-ray reflectance measurement, so that the receiving slit 18 regulates the scattering angle 2θ. In contrast, since the present invention can determine the incident angle accurately using the analyzer crystal 58, the aperture width of the receiving slit 18 is made wide as about 0.3 mm for instance. With the wide aperture, even when the position of the sample surface is out of alignment with the goniometer center, the reflected X-ray from the sample is not interrupted by the receiving slit. The receiving slit 18 in the present invention has no function of regulating the scattering angle 2θ but acts only as an aperture for interrupting scattering X-rays.

The incident X-ray 10 passes through the goniometer center O and the receiving slit 18, and is reflected by the analyzer crystal 58 to be detected by the X-ray detector 12. Only when the reflective surface of the analyzer crystal 58 is adjusted for the predetermined angle to the incident X-ray 10, the analyzer crystal 58 reflects the X-ray. With a combination of the analyzer crystal 58 using a Ge(220) plane and the incident X-ray 10 consisting of CuKα-ray, whose wavelength is 0.15406 nanometer, when the incident angle of the incident X-ray 10 is set to 22.65 degrees to the reflective surface of the analyzer crystal 58, the reflection occurs. The angle of the analyzer crystal 58 can be correctly adjusted, with the use of the fine adjustment mechanism shown in FIG. 9, so that the X-ray intensity detected by the X-ray detector becomes the maximum.

Next, as shown in FIG. 10B, the sample 16 is attached to the sample holder. Then, the position of the sample holder is adjusted so that the surface of the sample 16 coincides with the goniometer center O with the use of the usual half-split method. It is noted, however, that it is difficult to attain the perfect alignment within about one micrometer, coming to existence of an error δW between the surface of the sample 16 and the goniometer center.

Figure 12:
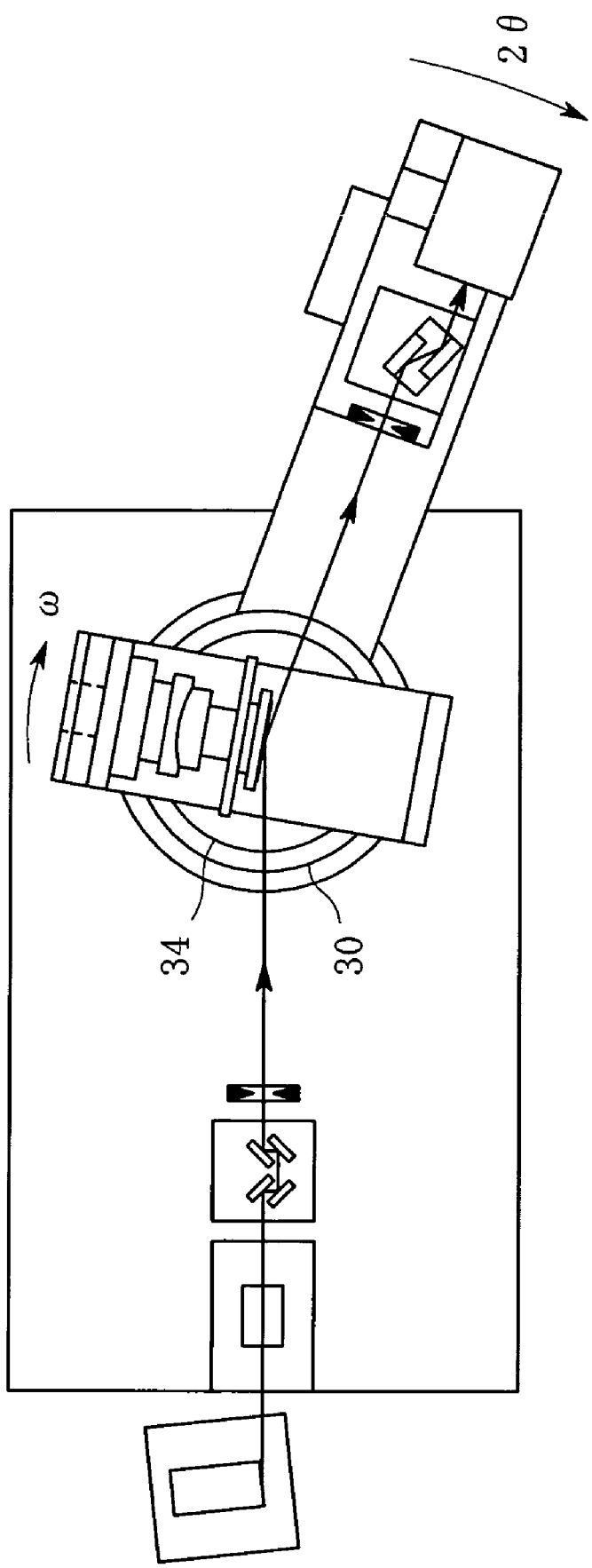
FIG. 12 is a plan view showing another state of the apparatus for X-ray reflectance measurement shown in FIG. 5.

Next, as shown in FIG. 12, the 2θ-turntable 30 is rotated in 2θ-rotation and the ω-turntable 34 is rotated in ω-rotation, for example, 2θ is set to 0.6 degree and ω is set to 0.3 degree which is the half of 0.6 degree. This value of 0.6 degree corresponds to the reference angle 2θr in the present invention. Although FIG. 12 shows large rotation angles for easy understanding, actual rotation angles are very small such as less than one degree as described above, because actual X-ray reflectance measurement is carried out for small incident angles.

FIG. 10C shows the condition in which the 2θ-turntable has been rotated by 0.6 degree, noting that the rotation angle is exaggerated in this figure too. The observed value 2θm for the angle of the 2θ-turntable is 0.6 degree. Under the condition, the angle of the ω-turntable, i.e., the rotation angle of the sample 16, is scanned in the vicinity of ω=0.3 degree to search for the optimum angle at which the X-ray intensity detected by the X-ray detector 12 becomes the maximum. The maximum X-ray intensity means that the reflected X-ray 20, which is generated in the condition in which the incident X-ray 10 is reflected by the surface of the sample 16 under specular reflection, is incident on the analyzer crystal at the predetermined correct angle.

It is very important, under the condition, that even if the above-described error δW exists and therefore the X-ray irradiation point P on the surface of the sample 16 is out of alignment with the goniometer center O, the angle of the reflected X-ray 20 to the incident X-ray 10, i.e., the real scattering angle 2θa is just equal to the observed value 2θm for the angle of the 2θ-turntable. Since the analyzer crystal 58 has been rotated by 2θm around the goniometer center O, the analyzer crystal 58 is to reflect only the X-ray which is inclined by 2θm with respect to the incident X-ray 10. Accordingly, the angle 2θa of the reflected X-ray 20, which passes via the analyzer crystal 58 and is detected by the X-ray detector 12, coincides perfectly with 2θm. After all, as indicated by formula (6) in FIG. 10C, 2θa is equal to 2θm. It is noted, however, that since the X-ray irradiation point P on the sample 16 is out of alignment with the goniometer center O, the real reflected X-ray 20 corresponds to the result of a translational movement of the reflected X-ray 21 which comes from the assumed irradiation point just on the goniometer center O. Therefore, the aperture width of the receiving slit 18 is made wide so as to take in such a reflected X-ray 20.

Since the observed scattering angle of the reflected X-ray 20 is exactly 2θm, the angle of the surface of the sample 16 with respect to the incident X-ray 10, i.e., the real incident angle ωa, becomes exactly the half of 2θm, based on the characteristic feature of the specular reflection. As 2θm has been set to 0.6 degree, ωa becomes exactly 0.3 degree. Thus, it becomes possible to exactly determine the incident angle ωa. The observed value ωa for the angle of the ω-turntable in this condition would be, in general, slightly different from 0.3 degree, the difference being dependent on the above-described error δW. Then, the measuring scale for the angle of the ω-turntable is corrected by being shifted so that the observed value ωm measured with the shifted measuring scale perfectly coincides with 0.3 degree. As a result, as for the current sample 16 attached to the sample holder, the observed value ωm for the angle of the ω-turntable is to perfectly coincide with the angle of the incident X-ray 10 with respect to the sample surface, i.e., the incident angle ωa, as indicated by formula (7) in FIG. 10C.

Figure 13:
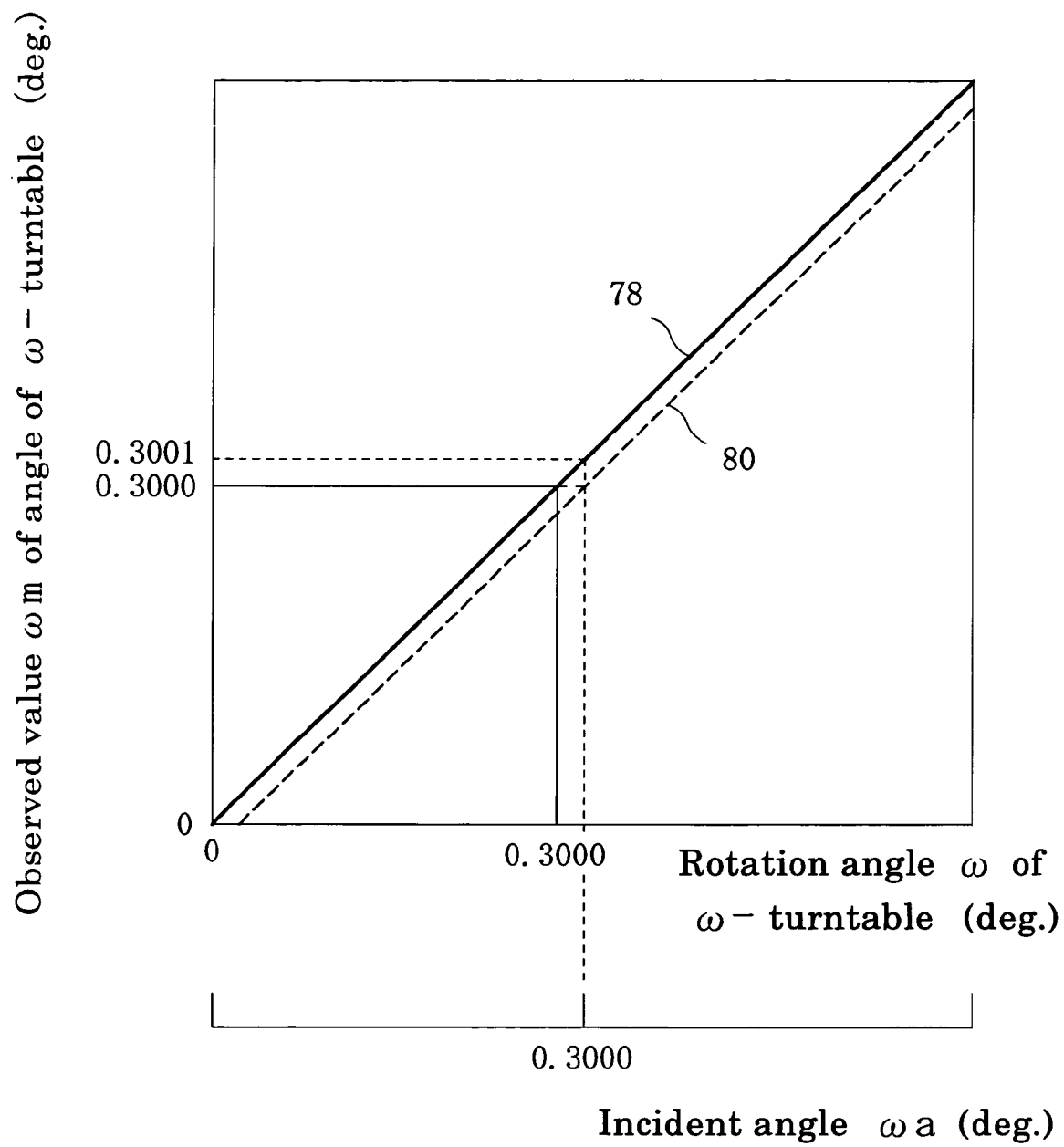
FIG. 13 is a graph indicating a corrective operation for the observed value of the ω-rotation.

FIG. 13 is a graph indicating a corrective operation described above: an observed value ωm for the angle of the ω-turntable in ordinate, while a rotation angle ω of the ω-turntable in upper abscissa and an incident angle ωa in lower abscissa. At the time of the production of the rotation drive mechanism for the ω-turntable, the rotation angle ω of the ω-turntable and its observed value ωm are consistent with one another. For instance, if the observed value ωm is 0.3000 degree, the rotation angle ω of the ω-turntable is 0.3000 degree too. Such a relationship between ωm and ω can be expressed by one characteristic curve 78. If ωm and ω are always consistent with one another at any angle, the characteristic curve 78 becomes a straight line having a gradient of 45 degrees.

It is assumed, in the above-described operation shown in FIG. 10C, that when the condition of ωa=0.3000 degree is realized, the observed value ωm becomes 0.3001 degree. If the characteristic curve 78 remains as it is, the observed value ωm is 0.3001 degree accordingly. In contrast, the characteristic curve 78 may be shifted downward so that the observed value becomes 0.3000 degree to make the corrected characteristic curve 80. With the corrected characteristic curve 80, the observed value ωm is to coincide with the incident angle ωa. The corrected characteristic curve 80 can be produced in a manner that the output value of the encoder for the ω-turntable may be shifted by a suitable amount to obtain a corrected output value.

In the above-described description, the corrective operation for the measuring scale is carried out for one point, i.e., 2θ=0.6 degree. This operation is based on the assumption that the characteristic curve 78 is one straight line. If the characteristic curve 78 is, however, out of the linearity, the corrective operation may be carried out for a plurality of 2θ values.

The angle for which the corrective operation is carried out, i.e., 2θ=0.6 degree, may be another angle. Since the specular reflection occurs at any angle as long as it is a low angle, the corrective operation may be carried out for any angle other than 0.6 degree. A suitable angle may be selected from angles within the angular range for which the actual X-ray reflectance curve will be measured.

Next, there will be described an operation for the X-ray reflectance measurement based on the corrected observed value ωm. FIG. 11 shows a condition in which the analyzer crystal 58 has been removed from the X-ray path after the corrective operation for the measuring scale for the angle of the ω-turntable. The analyzer crystal 58 is, as shown in FIG. 8, left below the X-ray path. The aperture width of the receiving slit 18 remains wide so that the reflected X-ray 20 can pass through the slit 18 even if the error δW of the sample position exists. The X-ray detector 12 has been returned to the original position. Now, the receiving optical system is rotated in 2θ-rotation while the sample 16 is rotated in ω-rotation, i.e., 2θ:ω=2:1, so that an X-ray reflectance can be measured based on the exact X-ray incident angle, ωa=ωm.

Figure 14:
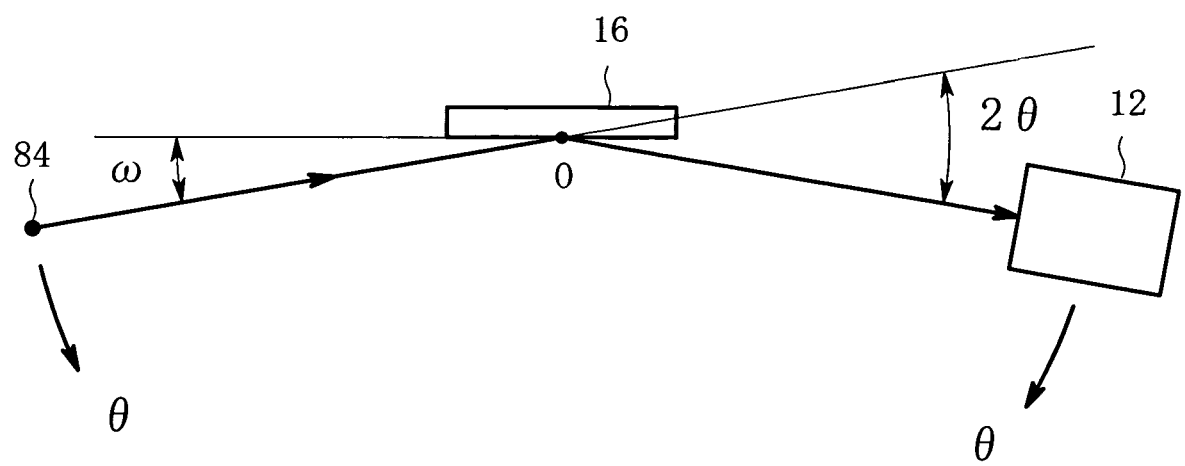
FIG. 14 is a plan view showing another X-ray optical system to which the present invention is applicable.

Although the above description uses an optical system in which the sample is rotated in ω-rotation while the receiving optical system is rotated in 2θ-rotation, the present invention is applicable to other optical systems. For instance, as shown in FIG. 14, there can be used an optical system in which the sample 16 remains stationary, and the X-ray source 84 is rotated in θ-rotation while the X-ray detector 12 is rotated in inverse θ-rotation. In this case, the corrected characteristic curve has to be obtained for the rotation angle of the X-ray source 84.

It should be noted that the correction of the measuring scale for the incident angle ω is limited to the current sample 16. When another sample is attached to the sample holder, another corrective operation for the measuring scale is required separately. Such an effort allows the incident angle ωa to be determined with high accuracy, so that the X-ray reflectance curve based on the accurate incident angle has high accuracy. Such an accurate X-ray reflectance curve is helpful in determining, with high accuracy, the thickness and the density of a thin film.

Figure 1A:
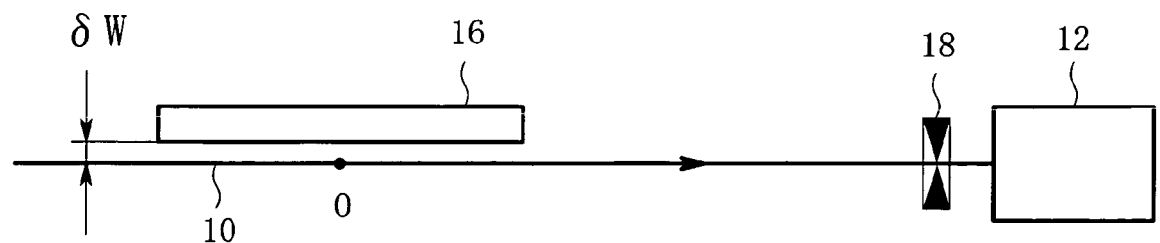
FIGS. 1A and 1B are plan views each showing an X-ray path in the prior-art method for X-ray reflectance measurement.
Figure 1B:
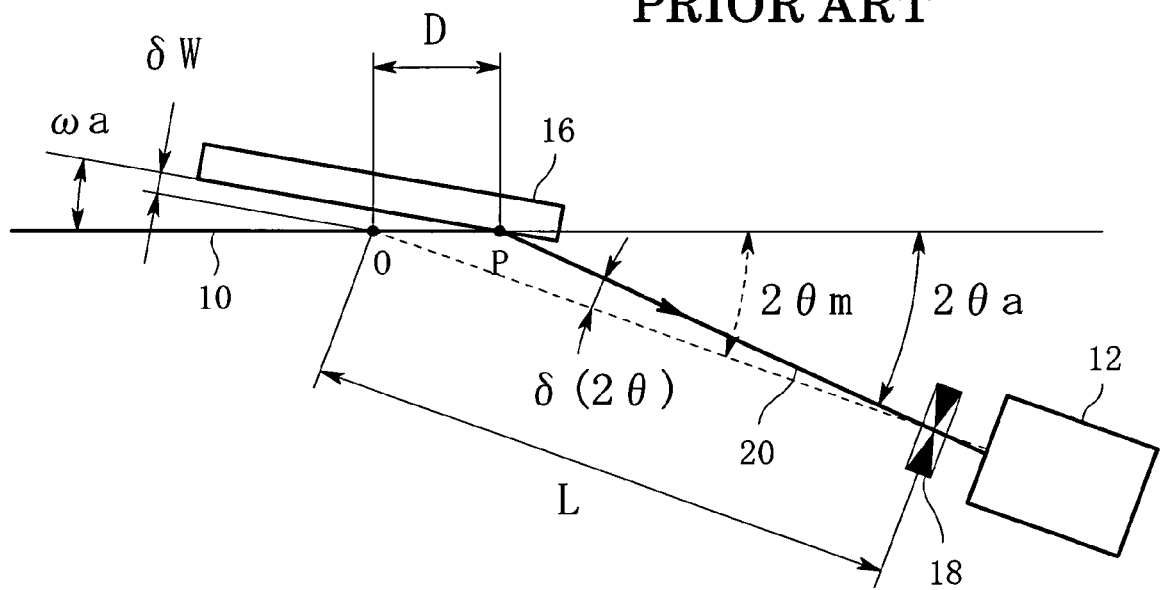
Figure 15:
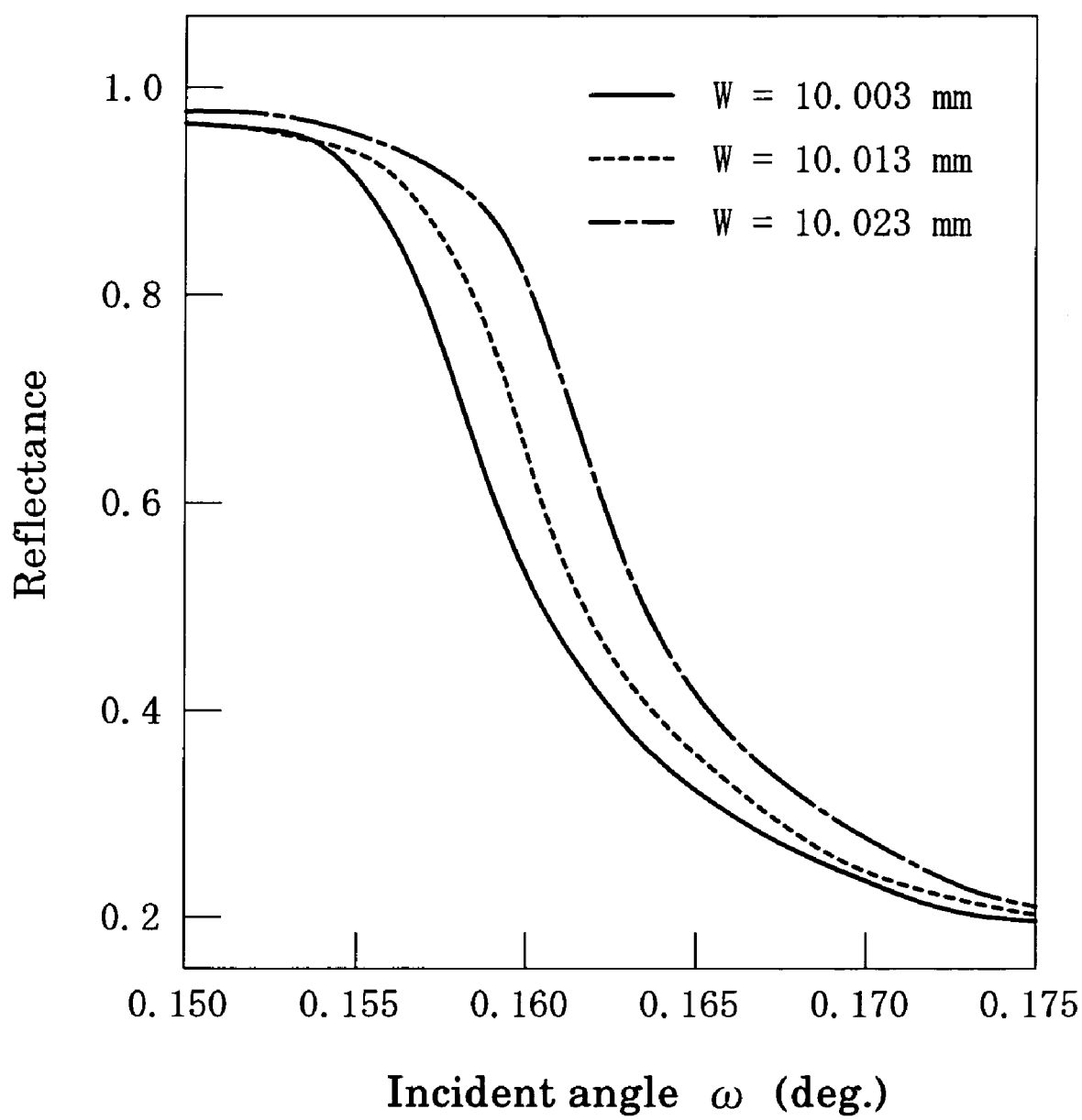
FIG. 15 is a graph of reflectance curves measured in the prior-art method.

Next, the measurement results will be described. FIG. 15 is a graph of reflectance curves of a porous interlayer insulating film on a silicon substrate measured in the prior-art method shown in FIG. 1, the graph indicating how reflectance curves vary with the positions of the sample. The graph shows parts of the reflectance curves in the vicinity of the critical angle of the total reflection. The surface of the sample almost coincides with the goniometer center, but is slightly out of alignment strictly. Three reflectance curves in FIG. 15 are obtained for three conditions in which the positions of the sample are different at 10-micrometer intervals. That is, the three positions of the sample are, in the W-direction in FIG. 4, 10.003 mm, 10.013 mm and 10.023 mm, noting that the zero point of the position has no special meaning. The incident angle ω in abscissa in the graph shown in FIG. 15 corresponds to the half of the observed value 2θm of the scattering angle. Since the incident angle ω in abscissa is different from the real incident angle ωa in response to the positional error of the sample, the three reflectance curves are disadvantageously different from each other even for the same sample in the prior-art method.

Figure 16:
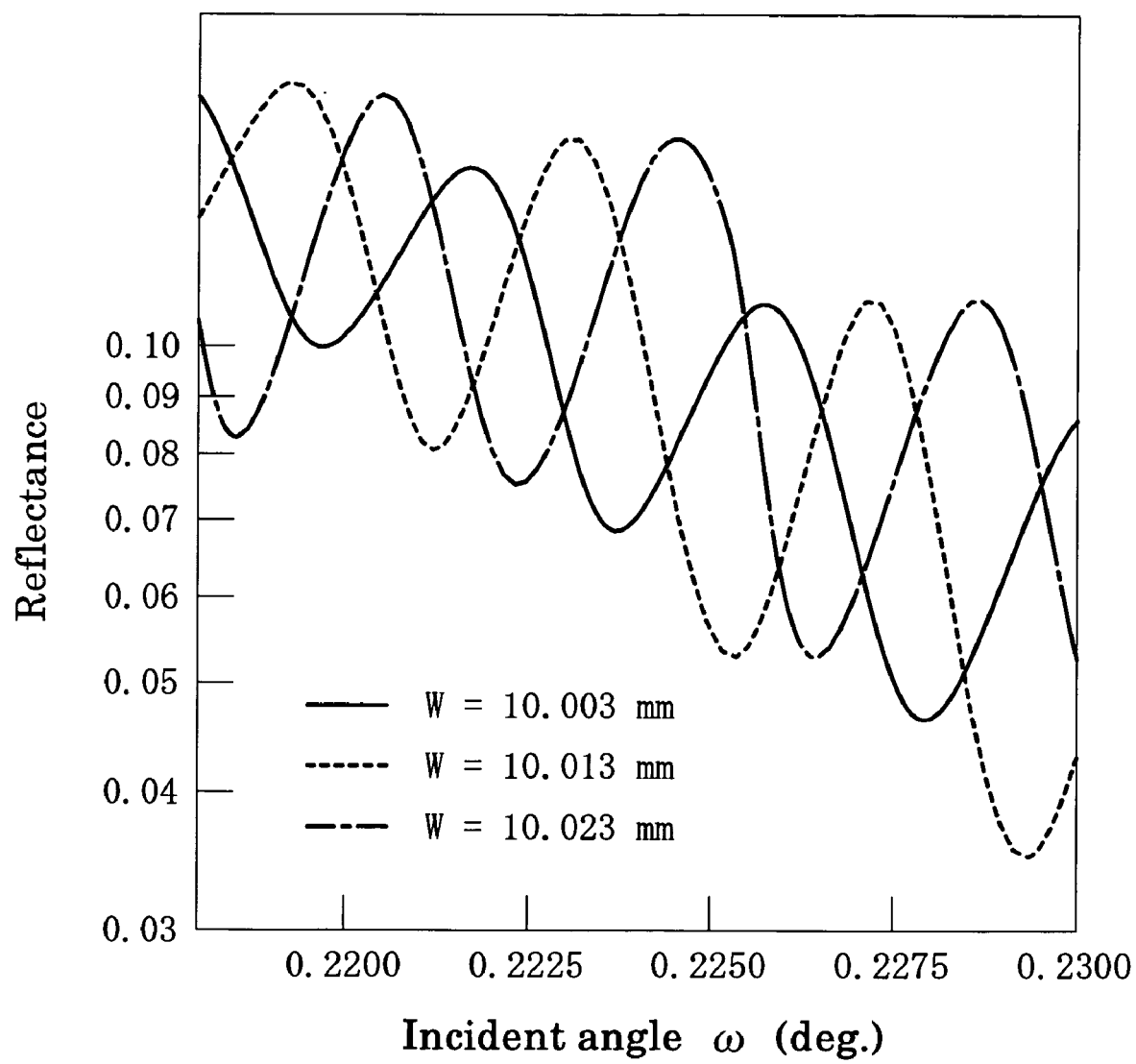
FIG. 16 is a graph showing enlarged parts near the interference oscillation patterns of the reflectance curves shown in FIG. 15.

FIG. 16 is a graph showing enlarged parts near the interference oscillation patterns, i.e., parts in the higher incident angle, of the three reflectance curves shown in FIG. 15. It is seen from the curves that appearance positions of the oscillation patterns in the reflectance curves are different from each other in response to the three positions of the sample. It would be possible tentatively to determine the thickness and the density of the sample with a fitting operation between the measured reflectance curve shown in FIGS. 15 and 16 and the theoretical curve. However, the analysis results for the thicknesses and densities would be different from each other because of the different reflection curves accordingly. FIG. 17 shows a table indicating densities and thicknesses which are determined based on the three reflectance curves. It is seen that the variation at 10-micrometer intervals in W causes differences in the number at the third digit from the top of the density values and the thickness values. Under the circumstances, anyone cannot verify what value is most reliable among the three values, i.e., what value corresponds to the minimum positional error of the sample.

Figure 18:
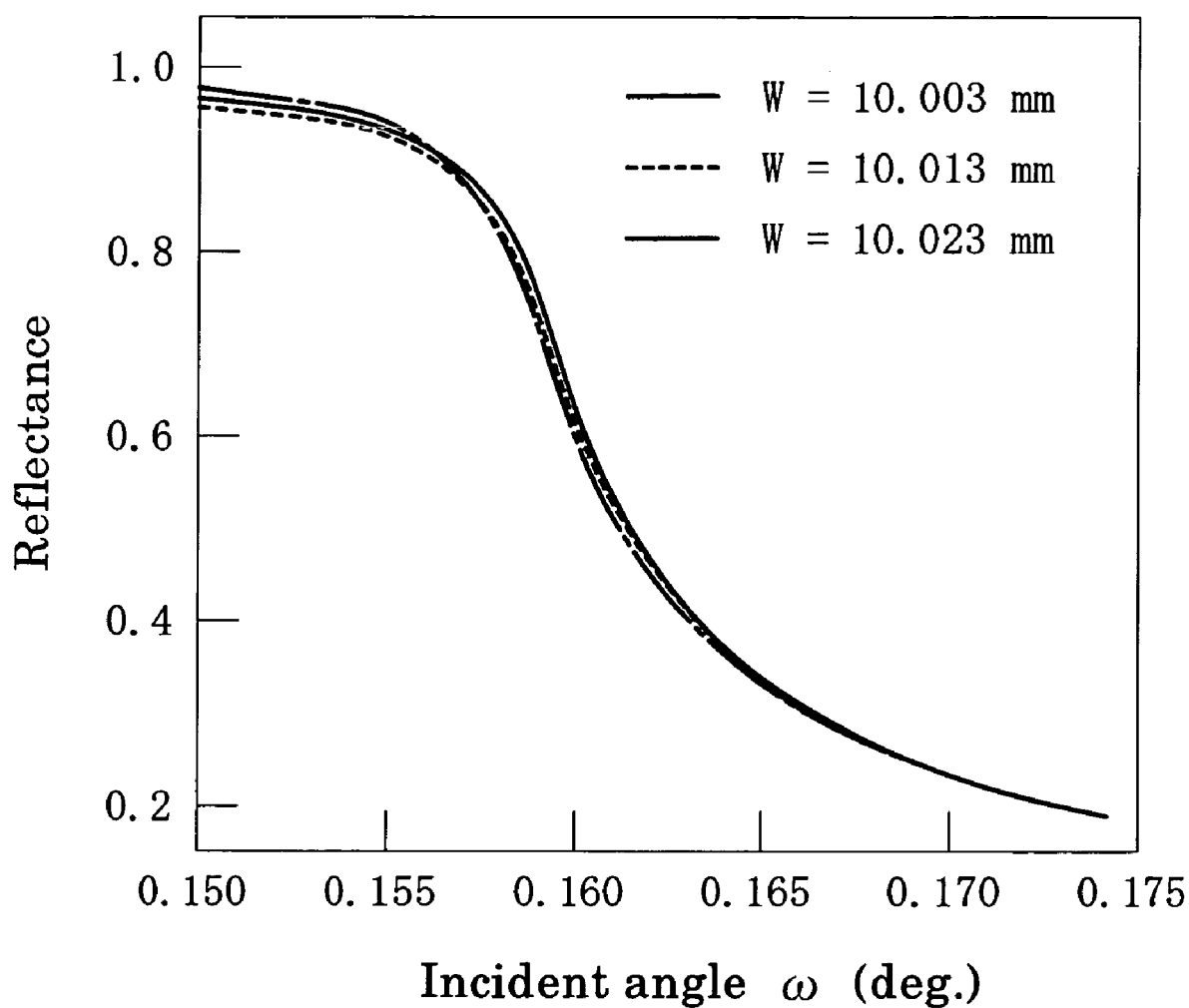
FIG. 18 is a graph of reflectance curves measured in the method according to the present invention.
Figure 19:
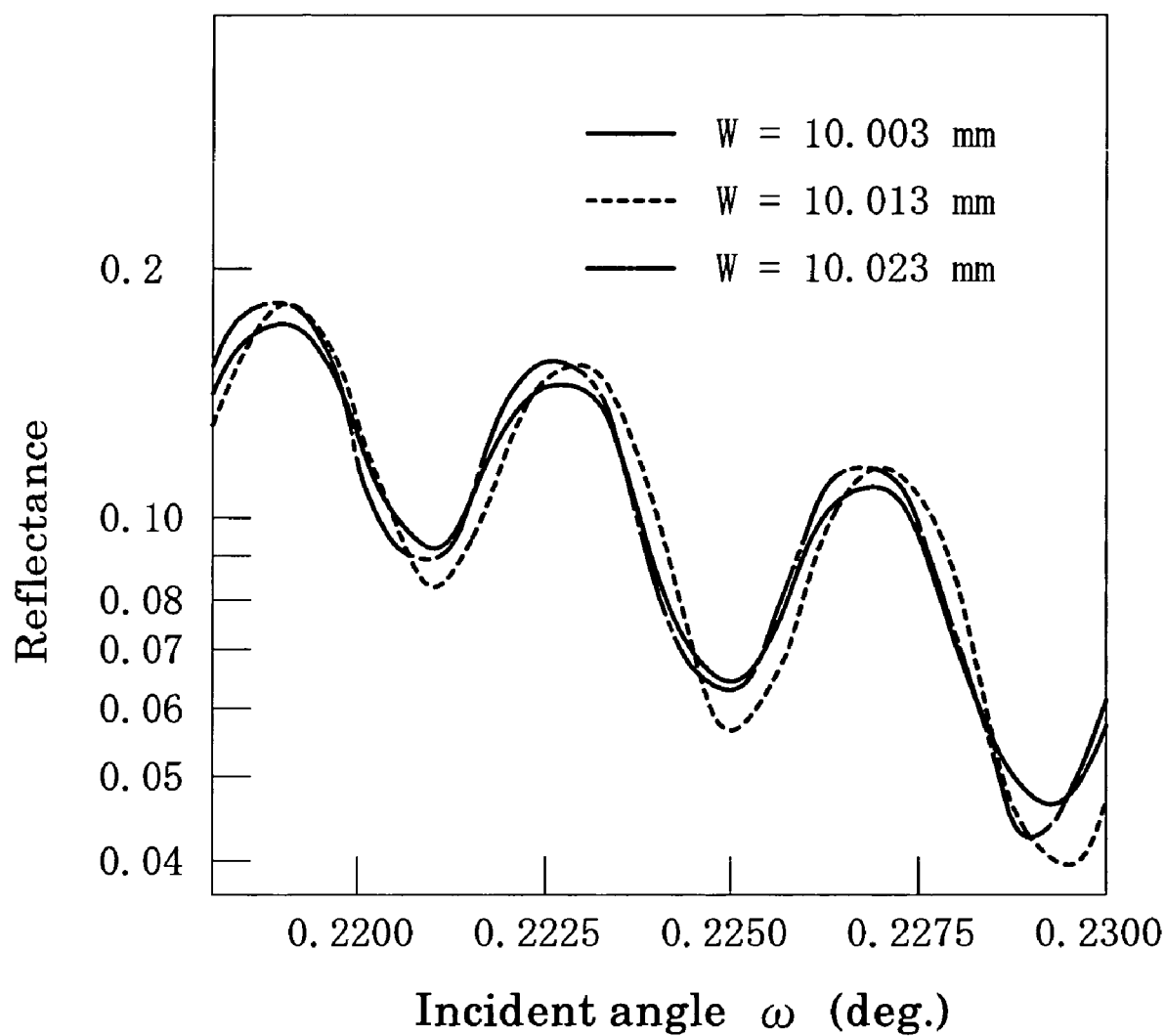
FIG. 19 is a graph showing enlarged parts near the interference oscillation patterns of the reflectance curves shown in FIG. 18.

Next, the measurement results based on the method according to the present invention will be described. FIG. 18 is a graph of reflectance curves, based on the method according to the present invention, measured for the three conditions in which the positions of the sample are different at 10-micrometer intervals, the graph being comparable to that shown in FIG. 15. It is seen from the graph of FIG. 18 that the critical angles of the total reflection almost coincides with each other regardless of the sample positions. The densities of the thin film determined by the critical angles are, as shown in FIG. 20, coincides with each other for the three conditions with accuracy of less than 0.4 percent. FIG. 19 is a graph showing enlarged parts near the interference oscillation patterns of the reflectance curves shown in FIG. 18, the graph being comparable to that shown in FIG. 16. It is also seen from the graph of FIG. 19 that the positions of the peaks and troughs of the oscillation patterns coincides with each other very well for the three conditions. As a result, as shown in FIG. 20, the thicknesses can be measured with accuracy within ±0.1 percent.

Figure 21:
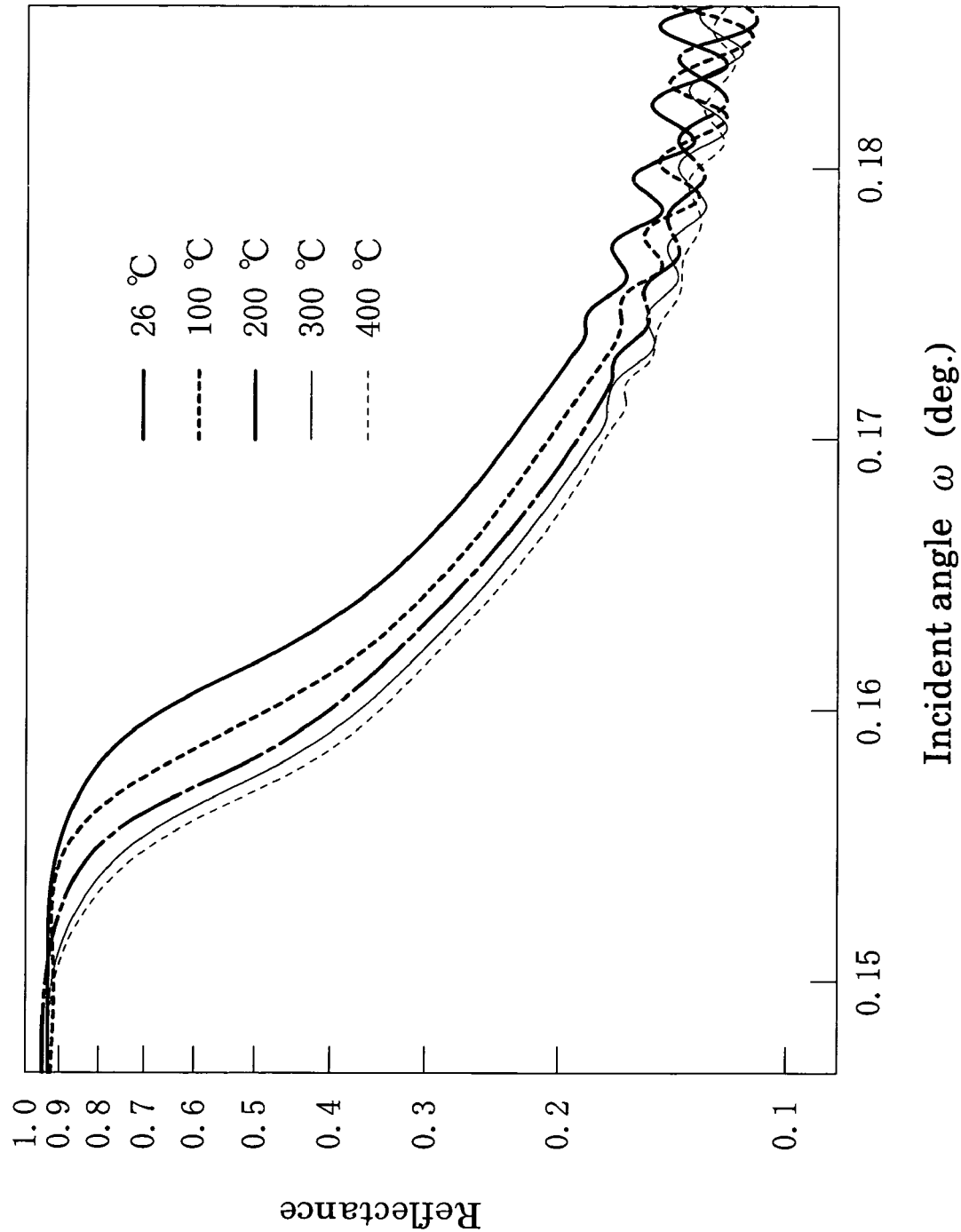
FIG. 21 is a graph showing reflectance curves for a porous interlayer insulating film for different temperatures, measured in the method according to the present invention.
Figure 22:
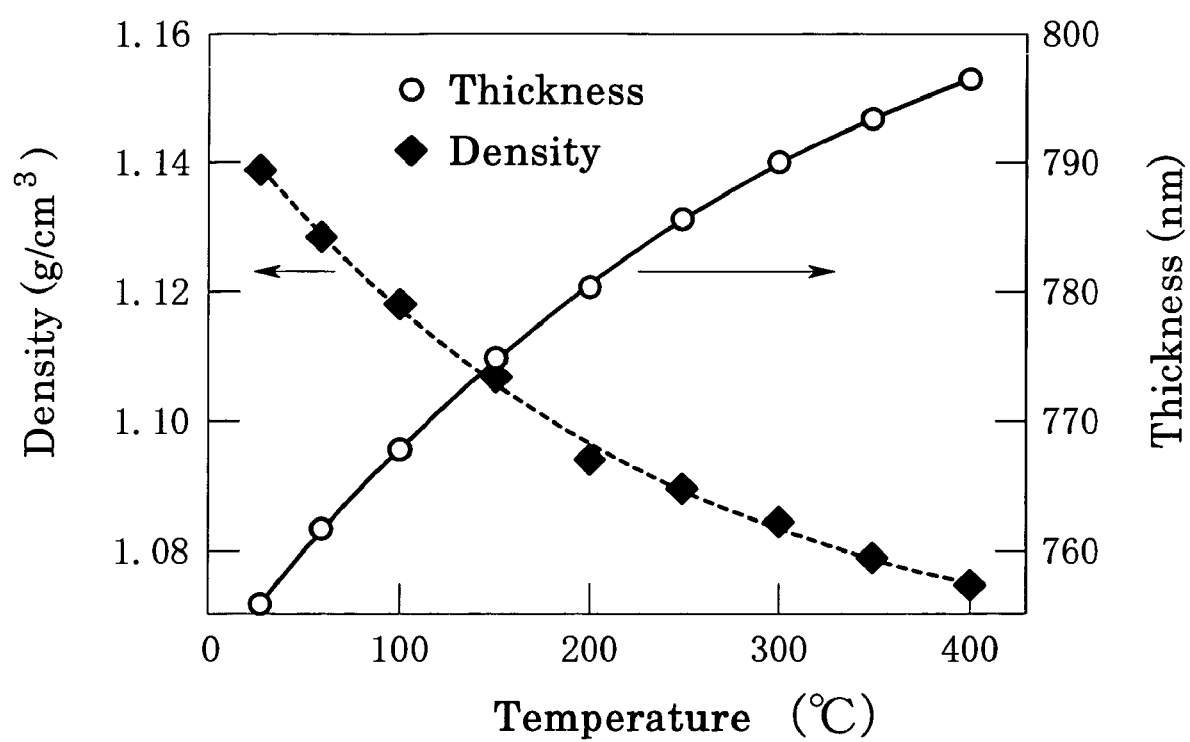
FIG. 22 is a graph of the temperature dependencies of densities and thicknesses which are determined based on the reflection curves shown in FIG. 21.
Figure 23:
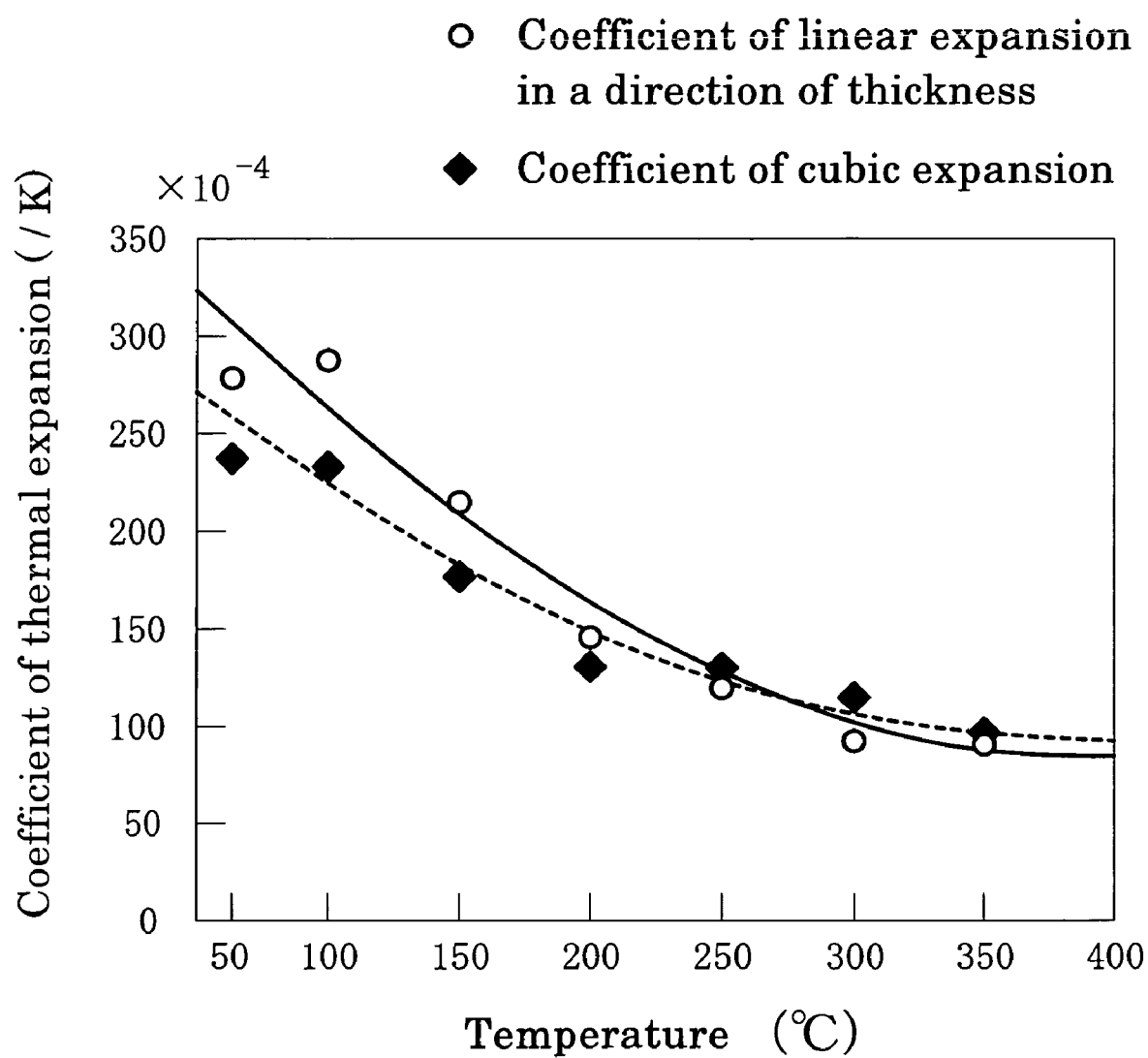
FIG. 23 is a graph of coefficients of thermal expansion which are determined based on the graph shown in FIG. 22.

As has been described above, the method has been established for determining the X-ray incident angle in the reflectance measurement with very high accuracy, e.g., less than 0.0003 degree in the embodiment shown FIG. 18. Since such high-precision measurement has been realized, it becomes possible to detect small variation in density and thickness, such as variation caused by thermal expansion of the thin film. FIG. 21 is a graph showing reflectance curves for a porous interlayer insulating film for different temperatures, measured in the method according to the present invention. It is clearly seen that the critical angle of the total reflection is shifted toward a lower angle with a rise of temperature, suggesting decrease of the thin film density with a rise of temperature. FIG. 22 is a graph of the temperature dependencies of densities and thicknesses which are determined based on the reflection curves shown in FIG. 21. It is clearly seen that, with a rise of temperature, the density gradually decreases because of the thermal expansion while the thickness gradually increases. The thus-obtained curves are differentiated with respect to temperature to obtain a coefficient of cubic expansion and a coefficient of linear expansion in a direction of the thickness. That is, the derivative of the temperature dependency of the density with respect to temperature corresponds to the coefficient of cubic expansion, while the derivative of the temperature dependency of the thickness with respect to temperature corresponds to the coefficient of linear expansion in a direction of the thickness. FIG. 23 is a graph of coefficients of thermal expansion which are determined as described above. It has been difficult in the conventional method to determine, with high accuracy, the density and the coefficient of thermal expansion in case of the thin film remaining as it is, but it becomes possible with the use of the method according to the present invention.

What is claimed is:

1. A method for X-ray reflectance measurement comprising:

providing an apparatus for X-ray reflectance measurement including: an X-ray source for generating an incident X-ray which is adapted to pass through a reference point; a sample holder for holding a sample to enable a surface of the sample to coincide with the reference point as precisely as possible; an X-ray detector for detecting an intensity of a reflected X-ray generated when the incident X-ray is reflected by the sample surface under specular reflection; incident-angle-changing means for changing an incident angle ω between the incident X-ray and the sample surface around the reference point which is a center of angle change; and scattering-angle-changing means for changing a scattering angle 2θ between the incident X-ray and a direction of the reflected X-ray around the reference point which is a center of angle change;

arranging an analyzer crystal in an X-ray path from the reference point to the X-ray detector, and adjusting a position of the X-ray detector with respect to the analyzer crystal so as to enable the reflected X-ray, having a certain wavelength, which has been reflected by the analyzer crystal to be properly detected by the X-ray detector;

setting the scattering angle 2θ to zero degrees using the scattering-angle-changing means to set a condition in which the incident X-ray passes through the reference point without being incident on the sample and in which the incident X-ray is reflected by the analyzer crystal and thereafter is detected by the X-ray detector, and adjusting an angle of the analyzer crystal with respect to the incident X-ray such that an X-ray intensity detected by the X-ray detector reaches a maximum;

setting the scattering angle 2θ to a predetermined reference angle 2θr using the scattering-angle-changing means without changing a positional relationship between the analyzer crystal and the X-ray detector, adjusting a position of the sample such that the sample surface coincides with the reference point as precisely as possible, irradiating the sample surface with the incident X-ray, adjusting the incident angle ω using the incident-angle-changing means such that an X-ray intensity of the reflected X-ray, which is reflected by the analyzer crystal and detected by the X-ray detector, reaches a maximum, and correcting a measuring scale for the incident angle ω such that an observed value of the incident angle ω becomes exactly half of the reference angle 2θr;

removing the analyzer crystal from the X-ray path and positioning the X-ray detector in a position to properly detect the reflected X-ray without the analyzer crystal being in the X-ray path;

measuring an X-ray reflectance of the sample, the measuring comprising: changing the incident angle ω to plural values based on the corrected measuring scale; irradiating the sample surface with the incident X-ray at each of the values of the incident angle ω; and detecting an intensity of the reflected X-ray by the X-ray detector at each of the values of the incident angle ω; and generating signals corresponding to the detected X-ray intensities.

2. A method according to claim 1, wherein the correcting the measuring scale for the incident angle ω comprises shifting a characteristic curve representative of a relationship between a value of the incident angle ω and the measuring scale of the incident angle ω.

3. A method according to claim 1, wherein the analyzer crystal comprises a channel-cut crystal having two reflective surfaces which are parallel to each other.

4. An apparatus for X-ray reflectance measurement comprising:

an X-ray source for generating an incident X-ray which is adapted to pass through a reference point;

a sample holder for holding a sample to enable a surface of the sample to coincide with the reference point as precisely as possible;

an X-ray detector for detecting an intensity of a reflected X-ray which is generated when the incident X-ray is reflected by the sample surface under specular reflection;

incident-angle-changing means for changing an incident angle ω between the incident X-ray and the sample surface around the reference point which is a center of angle change;

scattering-angle-changing means for changing a scattering angle 2θ between the incident X-ray and a direction of the reflected X-ray around the reference point which is a center of angle change;

an analyzer crystal which is adapted to be inserted in and removed from an X-ray path from the reference point to the X-ray detector;

means for: (i) adjusting a position of the X-ray detector so as to properly detect the reflected X-ray which has been reflected by the analyzer crystal when the analyzer crystal is inserted in the X-ray path, and (ii) adjusting a position of the X-ray detector so as to properly detect the reflected X-ray which has been reflected by the sample when the analyzer crystal is removed from the X-ray path; and means for adjusting an attitude angle of the analyzer crystal so as to allow the incident X-ray to be reflected by the analyzer crystal.

5. An apparatus according to claim 4, wherein the analyzer crystal comprises a channel-cut crystal having two reflective surfaces which are parallel to each other.

* * * * *